United States Patent [19]
Stojiljkovic et al.

[11] Patent Number: 6,123,942
[45] Date of Patent: *Sep. 26, 2000

[54] BACTERIAL HEMOGLOBIN RECEPTOR GENE

[75] Inventors: Igor Stojiljkovic; Magdalene So; Vivian Hwa, all of Portland; Fred Heffron, West Linn, all of Oreg.; Xavier Nassif, Paris, France

[73] Assignee: Oregon Health Sciences University, Portland, Oreg.

[*] Notice: This patent is subject to a terminal disclaimer.

[21] Appl. No.: 08/990,470

[22] Filed: Dec. 15, 1997

Related U.S. Application Data

[62] Division of application No. 08/326,670, Oct. 18, 1994, Pat. No. 5,698,438.

[51] Int. Cl.$^7$ .......................... A61K 39/02; A61K 39/095; A61K 39/00; C07K 1/00
[52] U.S. Cl. ..................... 424/190.1; 424/250.1; 424/184.1; 530/350; 530/825
[58] Field of Search .................. 536/23.1, 23.7; 530/825, 387.1, 388.2, 350; 424/234.1, 200.1, 93.4, 186.1, 150.1, 250.1, 190.1; 514/44, 898, 2; 435/7.2, 6, 252.3, 326

[56] References Cited

U.S. PATENT DOCUMENTS

| | | |
|---|---|---|
| 4,683,195 | 7/1987 | Mullis et al. . |
| 5,223,409 | 6/1993 | Ladner et al. . |
| B1 4,683,202 | 11/1990 | Mullis et al. . |

OTHER PUBLICATIONS

Archibald and DeVoe, (1979) FEMS Mirocbiol. Lett., 6, pp. 159–162.
Baggs and Neilands, (1991), Mircrobiol. Rev., 51, 509–518.
Braun and Hantke, (1991) in Winkelman (ed.) Handbook of Microbial Iron Chelates, pp. 107–138.
Calver et al., (1976) Can. J. Microbiol., 22, 832–838.
Cornelissen et al., (1993) J. Bacteriol., 174: pp. 5788–5797.
Correia et al., (1988) J. Biol. Chem., 263: 12194–12198.
Coulton and Pang, (1983) Curr. Microbiol., 9: pp. 93–98.
Dyer et al., (1987) Infect. Immun., 55: pp. 2171–275.
Fenno et al., (1993) Gene, 130: 81–90.
Gerlach et al., (1992) Infect. Immun., 60: 3253–3261.
Gotschlich et al., (1987) J. Exp. Med., 165: pp. 471–482.
Hames and Higgins, eds., (1985) Nucleic Acid Hybridization.
Harlow and Lane, (1988) Antibodis: A Laboratory Manual.
Heller et al., (1988) Gene, 64: pp. 147–153.
Henderson and Payne, (1994) J. Bacteriol, 176: pp. 3269–3277.
Hnatowich et al., (1983) Science, 220: pp. 613–615.
Holbien et al., (1981) Infect. Immun., 34: 120–125.
Jarosik et al., (1994) Infect. Immun., 62: pp. 2470–2477.
Kellog et al., (1963) J. Bacteriol, 85: 1274–1279.
Knight et al., (1992) Mol. Microbiol., 6: pp. 1565–1573.
Koebnik et al., (1993) Trends Microbiol., 6: pp. 1565–1573.
Lee and Hll, (1992) J. Gen. Microbiol., 138: 2647–2656.
Lee, (1994) Microbiol., 140: 1473–1480.
Lundrigan & Kadner, (1986) J. Biol. Chem., 261: pp. 10797–10801.
Martek and Lee, (1994) Infect. Immun., 62: 700–703.
McConville and Charles, (1979) J. Microbiol., 113: 165–168.
Meares et al., (1984) Anal. Biochem., 142: 68–78.
Mickelson et al., (1982) Infect. Immun., 35: pp. 915–920.
Nassif et al., (1993) Mol. Microbiol., 6: pp. 719–725.
Otto et al., (1992) Crit. Rev. Microbiol., 18: 217–233.
Pettersson et al., (1994) J. Bacteriol., 176: pp. 1764–1766.
Pettersson et al., (1993) Infect. Immun., 61: 4724–4733.
Postle, (1990) Mol. Microbiol., 133: pp. 891–898.
Riboli et al., (1991) Microb. Pathogen., 10: pp. 393–403.
Saiki et al., (1988) Science, 230: 1350–1354.
Sambrook et al., (1989) Molecular Clonong: A Laboratory Manual.
Schoffler and Braun, Molec. Gen. Genet., 217: pp. 378–383.
Schryvers and Morris, (1988) Infect. Immun., 56: pp. 1144–1149.
Schryvers and Morris, (1988) Mol. Microbiol., 2: 281–288.
Schryvers et al., (1989) Infect. Immun., 57(8): pp. 2425–2429.
Stojiljkovic et al., (1992) EMBO J., 11: pp. 4359–4367.
Stroebner and Payne, (1988) Infec. Immun., 56: pp. 2891–2895.
Struyve et al., (1991) J. Mol. Biol., 218: 141–148.
Walters, (1993) *Pharmaceutical Biotechnology*, pp. 165–174.
Weinberg. (1984) Physiological Rev., 64: pp. 65–102.
West and Sparling, (1985) Infect. Immun., 47: pp. 288–294.
Rudinger, (Jun. 1976), Peptide Hormones, pp. 1–7.
Stojiljkovic et al., (1995) Mol. Microbiol., 15: pp. 531–541.
Legrain et al., (1993) Gene, 130: pp. 81–90.
Bittner et al., (1995), Abstract Of The General Meeting Of The American Society For Microbiology, vol. 95, p. 227.

*Primary Examiner*—James C. Housel
*Assistant Examiner*—S. Devi
*Attorney, Agent, or Firm*—McDonnell Boehnen Hulbert & Berghoff

[57] ABSTRACT

The present invention relates to a novel bacterial hemoglobin receptor protein and genes that encode such a protein. The invention is directed toward the isolation, characterization, diagnostic and therapeutic use of a bacterial hemoglobin receptor protein, nucleic acid encoding such a protein, recombinant expression constructs comprising such nucleic acids and cells transformed therewith, and antibodies and epitopes of such hemoglobin receptor proteins. The invention relates particularly to hemoglobin receptor proteins and genes encoding such proteins from Neisseria species, especially *N. meningitidis*. Methods for the diagnostic and therapeutic use of the proteins, epitopes, antibodies and nucleic acids of the invention are also provided, including the use of the proteins, epitopes, antibodies and nucleic acids of the invention for the production of vaccines effectinve in providing immunization of a human against infection by pathogenic bacteria of Neisseria species.

1 Claim, 15 Drawing Sheets

FIG. 2A

```
        10                                                                60
AGAACTAGTGGATCCAATTTGGGCGCGGCGTTTTGTTCAAACACGCCCAAAAACTCGAT
             BamHI
                                                          110
TACAACGGCGAACACGGCCGCGCCACCTCCCTCCCGCATCCCGACGGCCCGCGGCAAACA
                                        160
CTGGGCGCGGCCTTCGTCGAGCATCTGAACGCTTTGAACCTGACTCCCGAAGCCGAAGCGGA
                            210
AGCCATTCAAGGGCGCGAAGCCCTTTGCATTCTACAAAGTCGTGTTGCGCGAAACCTT
                  260
CGGCTTGGCAGCCGATGCCGAAGCCCCCGAAGGTATGATGCCGCACAGGCACTAAAAAAT
                                                          360
AATCGAACCAAATAAACAAGGTCTCGGCATAGCTGTTTGCAGGGACCCTTTAATTACACGG
                                                  410
CGCGGCTTTGTTTACATGGATTACTGTCTTATTAAATATTAATGATTATCATAAAATCTA
                                         Fur-box           -10
TTATTCGCTAACCGATGAACATCCATACATCTTGAGTTGATAATATGAAACCATT
                                        SD            MetLysProLe
```

FIG. 2B

```
                  510
ACAAATGCTCCCTATCGCCCGCGCTGGTCGGCAGTATTTTCGGCAATCCGGTCTTTGCGGC
uGlnMetLeuProIleAlaAlaLeuValGlySerIlePheGlyAsnProValPheAlaAl
                  560

AGATGAAGCTGCAACTGAAACCACACCCGTTAAGGCAGAGGTAAAAGCAGTGCCGTTAA
aAspGluAlaAlaThrGluThrThrProValLysAlaGluValLysAlaValArgValLy
    610                                                    660

AGGCCAGGCGCAATGCGCCTGCGGGCCGTGTGAACGCGTCAACCTTAACCGTATCAAACAAGA
sGlyGlnArgAsnAlaProAlaAlaValGluArgValAsnLeuAsnArgIleLysGlnGl
                                                  710

AATGATACGCGACAACAAAGACTTGGTGCCGCTATTCCACCGATGTCGGCTTGAGGACAG
uMetIleArgAspAsnLysAspLeuValAlaArgTyrSerThrAspValGlyLeuSerAspSe
                             760

CGGCCGCCATCAAAAAGGCTTTGCTGTTCGCGGCGTGGAAGGCAACCGTGTCGGCGTGAG
rGlyArgHisGlnLysGlyPheAlaValArgGlyValGluGlyAsnArgValGlyValSe
                  810

CATAGACGGCGTAAACCTGCCTGATTCCGAAGAAAACTCGCTGTACGCCCGTTATGGCAA
rIleAspGlyValAsnLeuProAspSerGluGluAsnSerLeuTyrAlaArgTyrGlyAs
                                            860

CTTCAACAGCTCGCGCGTCTGTCTATCGACCCCGAACTCGTGCGCAACATCGACATCGTAAA
nPheAsnSerSerArgLeuSerIleAspProGluLeuValLeuValArgAsnIleValLy
```

FIG. 2C

```
     910                                                                                    960
      |                                                                                      |
AGGGGCGGACTCTTTCAATACCGGCAGCGCCCTTGGCGGCCGGTGTGAATTACCAAAC
 sGlyAlaAspSerPheAsnThrGlySerGlyAlaLeuGlyGlyGlyValAsnTyrGlnTh

CCTGCAAGGACGTGACTTACTGTTGCCTGAACGGCAGTTCGGCCGTGATGAAAAACGG
 rLeuGlnGlyArgAspLeuLeuLeuProGluArgGlnPheGlyValMetMetLysAsnGl
                                    1060

TTACAGCACGCCGTAACCGTGAATGGACAAATACCCTCGGTTTCGGCGTGAGCAACGACCG
 yTyrSerThrArgAsnArgGluTrpThrAsnThrLeuGlyPheGlyValSerAsnAspAr
                  1110

CGTGGATGCCGCTTTGCTGTATTCGCAACGGCCATGAAACTGAAAGCGCGGCAA
 gValAspAlaAlaLeuLeuTyrSerGlnArgArgGlyHisGluThrGluSerAlaGlyLy
                        1160

GCGTGGTTATCCGGTAGAAGGGTGCTGGTAGCGGAGCGAATATCCGTGGTTCTGCCGCGG
 sArgGlyTyrProValGluGlyAlaGlySerGlyAlaAsnIleArgGlySerAlaArgGl
         1210                                                       1260

TATTCCTGATCCGTCCCAACACAAATACCACAGCTTCTTGGGTAAGATTGCTTATCAAAT
 yIleProAspProSerGlnHisLysTyrHisSerPheLeuGlyLysIleAlaTyrGlnIl
                                        1310

CAACGACAACCACCGCATCGGCGCATCGGCTCAACGGTCAGCAGGGCATAATTACACCGGT
 eAsnAspAsnHisArgIleGlyAlaSerLeuAsnGlyGlnGlnGlyHisAsnTyrThrVa
```

FIG. 2D

```
                                          1360
                                            |
TGAAGAGTCTTACAACCTGCTTCTTATTGGCGTGAAGCTGACGATGTCAACAGACG
 l G l u S e r T y r A s n L e u L e u A l a S e r T y r T r p A r g G l u A l a A s p V a l A s n A r g A r
                             1410
                              |
GCGTAACACCAACCTCTTTTACGAATGGACGCCCGGAATCCGACCGGTTGTCTATGGTAAA
 g A r g A s n T h r A s n L e u P h e T y r G l u T r p T h r P r o G l u S e r A s p A r g L e u S e r M e t V a l L y
                             1460
                              |
AGCGGATGTCGATTATCAAAAAACCAAAGTATCTCGCGGTCAACTACAAAGGTTCGTTCCC
 s A l a A s p V a l A s p T y r G l n L y s T h r L y s V a l S e r A l a V a l A s n T y r L y s G l y S e r P h e P r
                             1510                                                        1560
                              |                                                            |
GATAGAGGATTCTTCCACCTTGACACGTAACTACAATCAAAAGGACTTGGATGAAATCTA
 o I l e G l u A s p S e r S e r T h r L e u T h r A r g A s n T y r A s n G l n L y s A s p L e u A s p G l u I l e T y
                             1610
                              |
CAACCCGCAGTATGGATACCCGCTTCAAACGCATTACCCTGCGTTTGGACAGCCATCCGTT
 r A s n A r g S e r M e t A s p T h r A r g P h e L y s A r g I l e T h r L e u A r g L e u A s p S e r H i s P r o L e
                             1660
                              |
GCAAACTCGGGGGGGGGGGACACCCGCTGTCGTTTAAAACTTTCGCCAGCCCGTGATTT
 u G l n L e u G l y G l y A r g H i s A r g L e u S e r P h e L y s T h r P h e A l a S e r A r g A s p P h
                             1710
                              |
TGAAAAACCTAAACCGGCGACGATTATTACTTCAGCGGCCCTGTTCGAACCACCAGCAG
 e G l u A s n L e u A s n A r g A s p A l a T h r I l e I l e L e u G l n A l a P r o V a l A l a A r g T h r T h r S e r S e
```

FIG. 2E

```
TATCCAGCATCCGGGTGAAAACCACCAACTACGGTTTCTCACTGTCTGACCAAATTCAATG
 IleGlnHisProValLysThrThrAsnTyrGlyPheSerLeuSerAspGlnIleGlnTr
         1810                         1860

GAACGACGTGTTCAGTAGCCGGCGGCAGGTATCCGTTACGATCATACCAAAATGACGCCTCA
pAsnAspValPheSerSerArgAlaGlyIleArgTyrAspHisThrLysMETThrProGl
         1910

GGAATTGAATGCCGAGTGTCATCGCTTGTGACAAAACACCGCTGCAGCCAACACTTATAA
nGluLeuAsnAlaGluCysHisAlaCysAspLysThrProProAlaAlaAsnThrTyrLy
         1960

AGGCTGGAGCGGGTTTGTCGGCTTGGCGGGGCGCAACTGAATCAGGCTTGGCCGTGTCGGTTA
sGlyTrpSerGlyPheValGlyLeuAlaAlaGluLeuAsnGlnAlaTrpArgValGlyTy
         2010

CGACATTACTTCCGGCTACCGTGTCCCCAATGCCTCCGAAGTGTATTTCACTTACAACCA
rAspIleThrSerGlyTyrArgValProAsnAlaSerGluValTyrPheThrTyrAsnHi
         2060

CGGTTCGGGTAATTGGCTGCCCAATCCCAACCTGAAAGCCGAGCGCACGACCACCCACAC
sGlySerGlyAsnTrpLeuProAsnProAsnLeuLysAlaGluArgThrThrThrHisTh
         2110                         2160

CCTCTCTCTGCAAGGCCCAGCGAAAAAGGTACTTTGGATGCCAACCTGTATCAAAGCAA
rLeuSerLeuGlnGlyArgSerGluLysGlyThrLeuAspAlaAsnLeuTyrGlnSerAs
```

FIG. 2F

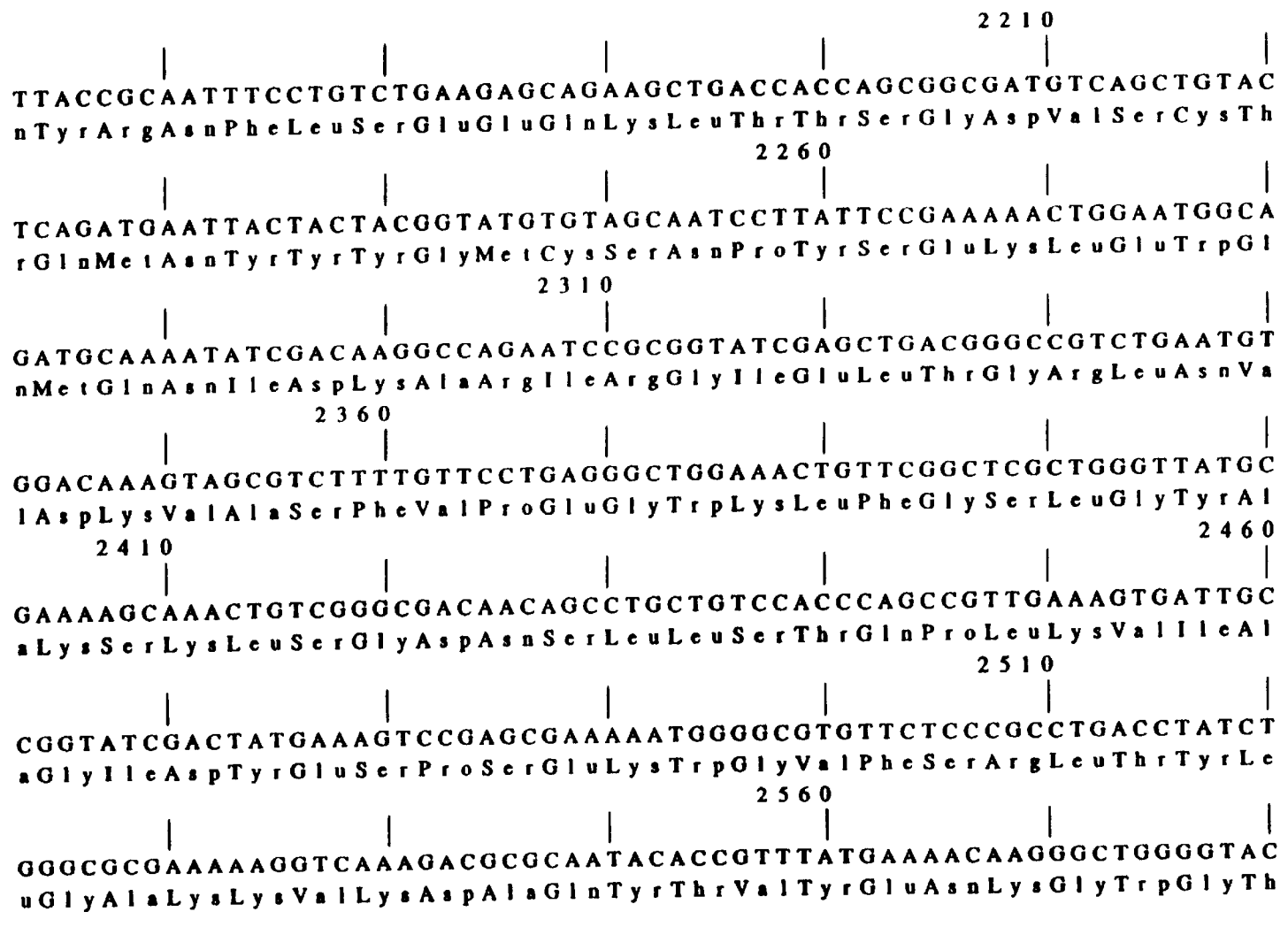

```
                                                  2210
TTACCGCAATTTCCTGTCTGAAGAGCAGAAGCTGACCACCAGCGGCGATGTCAGCTGTAC
nTyrArgAsnPheLeuSerGluGluGlnLysLeuThrThrSerGlyAspValSerCysTh
                                        2260
TCAGATGAATTACTACTACGGTATGTGTAGCAATCCTTATTCCGAAAAACTGGAATGGCA
rGlnMetAsnTyrTyrTyrGlyMetCysSerAsnProTyrSerGluLysLeuGluTrpGl
                              2310
GATGCAAAATATCGACAAGGCCAGAATCCGCGGTATCGAGCTGACGGGCCGTCTGAATGT
nMetGlnAsnIleAspLysAlaArgIleArgGlyIleGluLeuThrGlyArgLeuAsnVa
                    2360
GGACAAAGTAGCGTCTTTTGTTCCTGAGGGCTGGAAACTGTTCGGCTCGCTGGGTTATGC
lAspLysValAlaSerPheValProGluGlyTrpLysLeuPheGlySerLeuGlyTyrAl
   2410                                                 2460
GAAAAGCAAACTGTCGGGCGACAACAGCCTGCTGTCCACCCAGCCGTTGAAAGTGATTGC
aLysSerLysLeuSerGlyAspAsnSerLeuLeuSerThrGlnProLeuLysValIleAl
                                                  2510
CGGTATCGACTATGAAAGTCCGAGCGAAAAATGGGGCGTGTTCTCCCGCCTGACCTATCT
aGlyIleAspTyrGluSerProSerGluLysTrpGlyValPheSerArgLeuThrTyrLe
                                        2560
GGGCGCGAAAAAGGTCAAAGACGCGCAATACACCGTTTATGAAAACAAGGGCTGGGGTAC
uGlyAlaLysLysValLysAspAlaGlnTyrThrValTyrGluAsnLysGlyTrpGlyTh
```

FIG. 2G

```
             2610
              |
GCCTTGCAGAAAAAGGTAAAAGATTACCCGTGGCTGAACAAGTCGGCTTATGTGTTCGA
rProLeuGlnLysLysValLysAspTyrProTrpLeuAsnLysSerAlaTyrValPheAs
                   2660

TATGTACGGCTTCTACAACCGGTGAAAAACCTGACTTTGCGTGCAGGCGTATATAATGT
pMetTyrGlyPheTyrLysProValLysAsnLeuThrLeuArgAlaGlyValTyrAsnVal
     2710                                                 2760

GTTCAACCGCAAATACACCACTTGGGATTCCCTGCGCGGCCTGTATAGCTACAGCACCAC
lPheAsnArgLysTyrThrThrTrpAspSerLeuArgGlyLeuTyrSerTyrSerThrTh
                                          2810

CAACTCGGTCGACCCGCGATGGCAAGGCTTAGACCGGCTACCGCGCCCCAAGCCGTAATTA
rAsnSerValAspArgAspGlyLysGlyLeuAspArgTyrArgAlaProSerAlaAsnTy
                           2860

CGCCGTATCGCTGGAATGGAAGTTTTAATCTGGTATTATTGAATTAATCGCCTTGTTGAA
rAlaValSerLeuGluTrpLysPheSTOP
                       2910

AATTAAAGCCGTCCGAATTGTGTTCAAGAACTCATTCGGACGGTTTTTACCGAATCTGTG
                  2960

TGTGGGTTTATAGTGGATTAACAAAAATCAGGACAAGGGGACGAAGCCGCAGACAGTACA
```

FIG. 2H

```
3010
GATAGTACCGGAACCGATTCACTTGGTGAGACCCTTTGCAAAATTCCTTTCCCTCCCGACAG
                              ·······> IS1106        3110       3060

CCGAAACCCAAACACAGGTTTTCGGCTGTTTCGCCCCAAATACCTCCTAATTCTACCCA
                                                3160

AATACCCCCTTAATCCTCCCCGATAACCCGATAATCAGGCATCCCGGCGCCTTTAGGCGGCA
              3210

GCGGGGCGCACTTAACCTGTGTTGGCGGCTTTCAAAAGGTTCAAACACATCGCCTTCAGGTGC
                  3260

CTTTGCGCCACTCACTTTAATCAGTCCGAAATAGGCCCGGCGCATAGCAGAACTTACGG
     3310

TGCAGCGTACCGAAGCTT
              HindIII
```

FIG. 4A

```
TBP1M  MQQQHLFRNILCLSLMTALPVYA---ENVQAEQAQEKQLDTIQVKAKKQ        47
LBPA   MNKKHGFQLTLTALAVAAAFPSYAANPETAAPDAAQTQSLKEVTVRAAKV        50
HMBR   MKPLQMLPIAALVGSIFGN-PVFAADEAATETTPVKAE----VKAVR          43

TBP1M  KTRRDNEVTGLGKLVKSSDTLSKEQVLNIRDLTRYDPGIAVVEQGRGASS        97
LBPA   -GRRSKEATGLGKIAKTSETLNKEQVLGIRDLTRYDPGVAVVEQGNGASG        99
HMBR   KGQRNA-PAAVERV--NLNRIKQEMIRDNKDLVRYSTDVGLSDSGRHQK-        89

TBP1M  GYSIRGMDKNRVSLTVDGVSQIQSYTAQAALGGTRTAGSSGAINEIEYEN        147
LBPA   GYSIRGVDKNRVAVSVDGVAQIQAFTVQGSLSGYGGRGGSGAINEIEYEN        149
HMBR   GFAVRGVEGNRVGVSIDGVNLPDS--EENSLYARYGNFNSSRLS-IDPEL        136

TBP1M  VKAVEISKGSNSSEYGNGALAGSVAFQTKTAADIIGEGKQWGIQSKTAYS        197
LBPA   ISTVEIDKGAGSSDHGSGALGGAVAFRTKEAADLISDGKSWGIQAKTAYG        199
HMBR   VRNIDIVKQADSFNTGSGALGGGVYNQTLQGRDLLPERQFGVMMKNGYS         186

TBP1M  GKDHALTQSLALAGRSGGAEALLIYTKRRGREIIAHKDAGKGVQ-SFNRL        246
LBPA   SKNRQFMKSLGAGFSKDGWEGLLIRTERQGRETHPHGDIADGVAYGINRL        249
HMBR   TRNREWTNTLGFGVSNDRVDAALLYSQRRGHETESAG----                223
```

FIG. 4B

```
TBPIM  PICRFGNNTYT-DCTPRNIGGNGYYAAVQDNVRLGRWADVGAGIRYDYRS      601
LBPA   SVCGYIETLRSRKCVPRKINGSNIHISLNDRFSIGKYFDFSLGGRYDRKN      635
HMBR   ------------SSIQHPVKTTNYGFSLSDQIQWNDVFSSRAGIRYDHTK      460

TBPIM  THSED---------KSVSTGTHRNLSWNAGVVLKP--FTWMDLTYRASTGF      641
LBPA   FTTSE---------ELVRSGRYVDRSWNSGIVFKP--NRHFSLSYRASSGF      675
HMBR   MTPQELNAECHACDKTPPAANTYKGWSGFVGLAAQLNQAWRVGYDITSGY      510

TBPIM  RLPSFAEMYGWRA----GESLKTLDLKPEKSFNREAGIVFKGDFGNLEAS      687
LBPA   RTPSFQELFGIDIYHDYPKGWQRPALKSEKAANREIGLQWKGDFGFLEIS      725
HMBR   RVPNASEVY-FTYNHGSGNWLPNPNLKAERTTTHTLSLQGRSEKGTLDAN      559

TBPIM  YFNNAYRDLIAFGYET---RTQNGQTSASGDPGYR---------------      719
LBPA   SFRNRYTDMIAVADHKTKLPNQAGQLTEIDIRDYY---------------      760
HMBR   LYQSNYRNFLS---BEQKLTT-SGDVSCTQMNYYYGMCSNPYSEKLEWQM      605

TBPIM  -NAQNARIAGINILGKIDWHGVWGGLPDG--LYSTLAYNRIKVKDADIRA      766
LBPA   -NAQNMSLQGVNILGKIDWNGVYGKLPEG--LYTTLAYNRIKPKSVSNRP      807
HMBR   QNIDKARIRGIELTGRLNVDKVASFVPEGWKLFGSLGYAKSKLSG----      650
```

FIG. 4C

```
TBP1M   DRTFVTSYLFDAVQPSRYVLGLGYDHPDGIWGINTMFTYSKAKSVDE---      813
LBPA    GLSL-RSYALDAVQPSRYVLGFGYDQPEGKWGANIMLTYSKGKNPDE---      853
HMBR    DNSLLST------QPLKVIAGIDYESPSEKWGVFSRLTYLGAKKVKDAQY      694
                  .    *   *  .    *    .  *  . *

TBP1M   -LLGSQALLNGNANAKKAASRRTRPWYVTDVSGYYNIKKHLTLRAGVYNL      862
LBPA    -L---AYLAGDQK-RYSTKRASSSWSTADVSAYLNLKKRLTLRAAIYNI       897
HMBR    TVYENKGWGTPLQKKVKDYPWLNKSAYVFDMYGFYKPVKNLTLRAGVYNV      744
           .       .   .    *  .      .     . . ***** **

TBP1M   LNYRYVTWBNVRQ--TAGGAVNQHKNVGVYNRYAAPGRNYTFSLEMKF        908
LBPA    GNYRYVTWESLRQ--TAESTANRHGGDSNYGRYAAPGRNFSLALEMKF        943
HMBR    FNRKYTTWDSLRGLYSYSTTNSVDRDGKGLDRYRAPSRNYAVSLEWKF        792
         * . ***  .     .   .    . .  **  .**  *  **
```

BACTERIAL HEMOGLOBIN RECEPTOR GENE

This application is a divisional of U.S. patent application Ser. No. 08/326,670, filed Oct. 18, 1994, now U.S. Pat. No. 5,698,438.

This invention was made with government support under National Institute of Health grants R01 AI32493 and R01 AI22933. The government has certain rights to this invention.

BACKGROUND OF THE INVENTION

1. Field of the Invention

This invention relates to hemoglobin receptor genes and the proteins encoded therefrom of certain bacterial species, particularly species of Neisseria bacteria. More particularly, this invention relates to hemoglobin receptor genes, polypeptides and peptides useful for preparing vaccines and antibodies against Neisseria, and methods and means for producing such peptides and polypeptides in vitro. Also provided are diagnostic and therapeutic methods and reagents useful in detecting and treating Neisseria infection and methods for developing novel and effective anti-Neisseria agents.

2. Background of the Invention

The Neisseria comprise a genus of bacteria that includes two gram-negative species of pyogenic cocci pathogenic for humans: *Neisseria meningitidis* and *Neisseria gonorrhoeae*. *N. meningitidis* is a major cause of bacterial meningitis in humans, especially children. The disease characteristically proceeds from asymptomatic carriage of the bacterium in the nasopharynx to invasion of the bloodstream and cerebrospinal fluid in susceptible individuals.

*Neisseria meningitidis* is one of the leading causes of bacterial meningitis in children and healthy adults in the world. The severity of the disease is epitomized by the ability of meningococci to cause the death of previously healthy individuals in less than 24 hours. *N. meningitidis* has a polysaccharide capsule whose diversity of component antigenic polysaccharide molecules has resulted in the classification of ten different serogroups. Of these, group A strains are the classic epidemic strains; group B and C are generally endemic strains, but C occasionally causes an epidemic outbreak. All known group A strains have the same protein antigens on their outer membranes, while group B strains have a dozen serotype or groupings based on the presence of principal outer membrane protein antigens (as opposed to polysaccharides).

Survival of a pathogen such as *N. meningitidis* in a host depends on its ability to overcome a battery of host defense mechanisms. One nonspecific host defense mechanism against microbial intruders is to limit the availability of iron in tissues (Weinberg. 1984, *Physiological. Rev.* 64: 65–102), because iron is a necessary nutrient for most microbial pathogens. The vast majority of iron in the human adult is located intracellularly in the form of haemoglobin (76%) or ferritin (23%). The remainder can be found extracellularly bound to host iron-binding proteins such as transferrin and lactoferrin (Otto et al., 1992, *Crit. Rev. Microbiol.* 18: 217–233).

Pathogenic bacteria have adapted to this iron-limiting environment by developing highly specific and effective iron assimilation systems. A large number of these bacteria secrete siderophores, small, non-protein iron chelators which, due to their extremely high affinity for iron (III), scavenge trace amounts of iron(III) from the environment and shuttle the iron back to the bacterial cell (Baggs and Neilands, 1987, *Microbiol. Rev.* 51: 509–518; Braun and Hantke, 1991, in Winkelmann (ed.), *Handbook of Microbial Iron Chelates*, CRC Press: Boca Raton, Fla., pp. 107–138.).

Alternatively, some bacterial pathogens, like Neisseriae species (Archilbald and DeVoe, 1979, *FEMS Microbiol. Lett.* 6: 159–162; Mickelson et al., 1982, *Infect. Immun.* 35: 915–920; Dyer et al., 1987, *Infect. Immun.* 55: 2171–2175), *Haemophilus influenzae* (Coulton and Pang, 1983, *Curr. Microbiol.* 9: 93–98; Schryvers, 1988, *Mol. Microbiol.* 2: 467–472; Jarosik et al., 1994, *Infect. Immun.* 62: 2470–2477), *Vibrio cholerae* (Stoebner and Payne, 1988, *Infect. Immun.* 56: 2891–2895; Henderson and Payne, 1994, *J. Bacteriol.* 176: 3269–3277), Yersiniae (Stojiljkovic and Hantke, 1992, *EMBO J.* 11: 4359–4367) and *Actinobacillus pleuropneumoniae* (Gerlach et al., 1992, *Infect. Immun.* 60: 3253–3261) have evolved more sophisticated mechanisms to sequester iron from the host. These pathogens can directly bind host's iron-binding proteins such as lactoferrin, transferrin, and haem-containing compounds, and use them as sole sources of iron.

The importance of iron in the virulence of *N. meningitidis* was demonstrated by in vivo studies using mice as the animal model system (Calver et al., 1976, *Can. J. Microbiol.* 22: 832–838; Holbien et al., 1981, *Infect. Immun.* 34: 120–125). Specific iron-regulated outer membrane receptors have been shown to be involved in the binding and the utilization of lactoferrin- and transferrin-iron in Neissenae (Schryvers and Morris, 1988, *Infect. Immun.* 56: 1144–1149 and *Mol. Microbiol.* 2: 281–288; Legrain et al., 1993, *Gene* 130: 81–90; Pettersson et al., 1993, *Infect. Immun.* 61: 4724–4733 and 1994, *J. Bacteriol.* 176: 1764–1766). These receptors share significant amino acid similarity and, most probably, also the mechanism of iron internalization, with receptors for siderophores and vitamin B12 of other Gram-negative bacteria (Cornelissen et al., 1993, *J. Bacteriol.* 174: 5788–5797). In contrast, the mechanism by which Neisseriae utilize hemoglobin- and hemin-iron as well as the components involved have so far not been described.

Recently, several proteins with hemoglobin-binding and/or hemin-binding activities have been identified in total membranes of iron-limited *N. meningitidis* and *N. gonorrhoeae*.

Lee and Hill, 1992, *J. gen. Microbiol.* 138: 2647–2656 disclose the specific hemoglobin binding by isolated outer membranes of *N. meningitidis*.

Martek and Lee, 1994, *Infect. Immun.* 62: 700–703 disclosed that acquisition of heme iron by *N. meningitidis* does not involve meningococcal transferrin-binding proteins.

Lee, 1994, *Microbiol.* 140: 1473–1480 describes the biochemical isolation and characterization of hemin binding proteins from *N. meningitidis*.

The precise role of these proteins in hemin and/or hemoglobin utilization remains unclear at present, although these proteins are likely to be components of a hemin-utilization system in *N. meningitidis*.

The dependence on host iron stores for Neisseria growth is a potentially useful route towards the development of novel and effective therapeutic intervention strategies. Historically, infections of both *N. meningitidis* and *N. gonorrhoeae* were treated chemoprophylactically with sulfonamide drugs. However, with the development of sulfonamide-resistant strains came the necessity of using alternative modes of therapy such as antibiotic treatment. More recently, the drug treatment of choice includes the administration of high grade penicillin. However, the success of antimicrobial treatment is decreased if therapy is not initiated early after infection.

Gonococcal infection has also been treated with penicillin, ampicillin, or amoxicillin, tetracycline hydrochloride, and spectinomycin. Unfortunately, because the incidence of infections due to penicillinase-producing bacteria has increased, several new, more expensive β-lactam antibiotics have been used in treatment. Despite the fact that existing antibiotics have decreased the serious consequences of gonorrhea, their use has not lowered the incidence of the infection in the general population.

Prevention of meningococcal disease has been attempted by chemoprophylaxis and immnunoprophylaxis. At present, rifampin and minocycline are used, but only for humans in close contact with an infected person as this treatment has a number of disadvantages. The only commercially available vaccine against meningococcal meningitis has as its major component the bacterial polysaccharide capsule. In adults this vaccine protects against serogroups A, C, Y and W135. It is not effective against serogroup B, and is ineffective in children against serogroup C. Thus far, immunoprophylatic preventive treatment has not been available for N. gonorrhoeae.

Thus, what is needed are better preventative therapies for meningococcal meningitis and gonorrhea including more effective, longer lasting vaccines which protect across all of the serogroups of N. meningitidis and all the serotypes of N. gonorrhoeae. In addition, better methods are need to treat meningococcal and gonococcal infection.

SUMMARY OF THE INVENTION

The present invention relates to the cloning, expression and functional characterization of a bacterial hemoglobin receptor protein. Specifically, the invention relates to such a hemoglobin receptor protein from Neisseria species, in particular Neisseria meningitidis. The invention comprises a nucleic acid having a nucleotide sequence encoding a novel bacterial hemoglobin receptor protein. Also provided by this invention is the deduced amino acid sequence of the cognate hemoglobin receptor protein of this bacterial gene.

The invention provides nucleic acids, nucleic acid hybridization probes, recombinant expression constructs capable of expressing the hemoglobin receptor protein of the invention in cultures of transformed cells, preferably bacterial cells, and such cultures of transformed bacterial cells that express the hemoglobin receptor protein of the invention. The invention also provides gene knockout vectors for inactivating the hemoglobin receptor protein gene in cells, particularly cells of Neisseria species, via, for example, homologous recombination and other mechanisms, and cultures of such hemoglobin receptor protein null mutant cells.

The invention also provides homogeneous preparations of the bacterial hemoglobin receptor proteins of the invention, as well as antibodies against and epitopes of the hemoglobin receptor protein. Methods for characterizing this receptor protein and methods for using the protein in the development of agents having pharmacological uses related to this receptor, particularly bactericidal and bacteriostatic uses, are also provided by the invention.

In other embodiments of this invention are provided diagnostic methods and reagents encompassing the use of the anti-Neisseria hemoglobin receptor protein antibodies of the invention. Still further embodiments provided herein include therapeutic methods and reagents encompassing the use of the anti-Neisseria hemoglobin receptor protein antibodies of the invention. Even more embodiments include diagnostic methods and reagents encompassing the use of the Neisseria hemoglobin receptor protein-encoding nucleic acids of the invention, as sensitive probes for the presence of Neisseria infection using nucleic acid hybridization techniques and/or in vitro amplification methodologies. Yet additional embodiments of the invention include therapeutic methods and reagents encompassing the use of the Neisseria hemoglobin receptor protein-encoding nucleic acids of the invention, comprising recombinant expression constructs engineered to produce antisense transcripts of the Neisseria hemoglobin receptor gene and fragments thereof, as well as recombinant knockout vectors of the invention. The invention also provides the Neisseria hemoglobin receptor protein and epitopes thereof as components of vaccines for the development of non-disease associated immunity to pathological infection with bacteria of Neisseria species.

In a first aspect, the invention provides a nucleic acid having a nucleotide sequence encoding a bacterial hemoglobin receptor protein gene. In a preferred embodiment, the bacterial hemoglobin receptor protein gene is isolated from bacteria of Neisseria species. In a particularly preferred embodiment, the hemoglobin receptor protein gene is isolated from Neisseria meningitidis. In a particular example of this embodiment, the nucleic acid comprises a 3.3 kilobase (kb) BamHI/HindIII fragment of N. meningitidis genomic DNA. In this embodiment, the nucleotide sequence comprises an open reading frame of 2376 nucleotides of N. meningitidis genomic DNA encoding 792 amino acids comprising the hemoglobin receptor gene. In this embodiment of the invention, the nucleotide sequence of the N. meningitidis hemoglobin receptor gene is the sequence depicted in FIGS. 2A–2H (SEQ ID No:1). It will be understood that the N. meningitidis gene as disclosed herein is defined, insofar as is necessary, by the amino acid sequence of the protein encoded therein, said amino acid sequence being represented in FIGS. 2A–2H (SEQ.ID No.:2). Thus, it will be understood that the particular nucleotide sequence depicted in FIGS. 2A–2H (SEQ. ID. No.:1) is but one of a number of equivalent nucleotide sequences that encode the hemoglobin receptor protein, due to the degeneracy of the genetic code, and that all such alternative, equivalent nucleotide sequences are hereby explicitly encompassed within the disclosed nucleotide sequences of the invention. Also included herein are any mutant or allelic variations of this nucleotide sequence, either naturally occurring or the product of in vitro chemical or genetic modification. Each such variant will be understood to have essentially the same nucleotide sequence as the nucleotide sequence of the corresponding N. meningitidis hemoglobin receptor protein disclosed herein.

The invention also provides a bacterial hemoglobin receptor protein. In a preferred embodiment, the bacterial hemoglobin receptor protein is isolated from bacteria of Neisseria species. In a particularly preferred embodiment, the hemoglobin receptor protein is isolated from Neisseria meningitidis. In a particular example of this embodiment, the protein comprises an amino acid sequence of 792 amino acids. In this embodiment of the invention, the amino acid sequence of the N. meningitidis hemoglobin receptor protein is the sequence depicted in FIGS. 2A–2H (SEQ ID No:2). Also encompassed within the scope of this invention are related bacterial hemoglobin receptor proteins, particularly such proteins isolated from Neisseria species, having essentially the same amino acid sequence and substantially the same biological properties as the hemoglobin receptor protein encoded by the N. meningitidis nucleotide sequence described herein.

In another aspect, the invention provides a homogeneous preparation of a 85.5 kiloDalton (kD) bacterial hemoglobin receptor protein or derivative thereof, said size being understood to be the size of the protein before any post-translational modifications thereof. Also provided is a 90 kD embodiment of the receptor as determined by sodium dodecyl sulfate/ polyacrylamide gel electrophoresis under reducing conditions. In a preferred embodiment, the bacterial hemoglobin receptor protein is isolated from bacteria of Neisseria species. In a particularly preferred embodiment, the hemoglobin receptor protein is isolated from *Neisseria meningitidis*. In this embodiment, the amino acid sequence of the bacterial hemoglobin receptor protein or derivative thereof preferably is the amino acid sequence of the *N. meningitidis* hemoglobin receptor protein shown in FIGS. 2A–2H (SEQ ID No:2).

This invention provides nucleotide probes derived from the nucleotide sequence herein provided. The invention includes probes isolated from either complementary DNA (cDNA) copies of bacterial messenger RNA (mRNA) or bacterial genomic DNA (gDNA), as well as probes made synthetically with the sequence information derived therefrom. The invention specifically includes but is not limited to oligonucleotide, nick-translated, random primed, or in vitro amplified probes made using cDNA or genomic clone embodying the invention, and oligonucleotide and other synthetic probes synthesized chemically using the nucleotide sequence information of cDNA or genomic clone embodiments of the invention.

It is a further object of this invention to provide such nucleic acid hybridization probes to detect the presence of bacteria of Neisseria species, particularly *N. meningitidis*, in a biological sample in the diagnosis of a Neisseria infection in a human. Such a biological sample preferably includes blood, urine, semen, mucus, cerebrospinal fluid, peritoneal fluid and ascites fluids, as well as cell scrapings from the epithelium of the mouth, urethrae, anus and rectum, and other organs.

The present invention also includes peptides encoded by the nucleotide sequences comprising the nucleic acid embodiments of the invention. The invention includes either naturally occurring or synthetic peptides which may be used as antigens for the production of hemoglobin receptor protein-specific antibodies. The invention also comprises such antibodies, preferably monoclonal antibodies, and cells and cultures of cells producing such antibodies.

Thus, the invention also provides antibodies against and epitopes of bacterial hemoglobin receptor proteins of the invention. It is an object of the present invention to provide antibodies that are immunologically reactive to the bacterial hemoglobin receptor proteins of the invention. It is a particular object to provide monoclonal antibodies against these bacterial hemoglobin receptor proteins. In a preferred embodiment, antibodies provided are raised against bacterial hemoglobin receptor protein isolated from bacteria of Neisseria species. In a particularly preferred embodiment, such antibodies are specific for the hemoglobin receptor protein isolated from *Neisseria meningitidis*.

Hybridoma cell lines producing such antibodies are also objects of the invention. It is envisioned that such hybridoma cell lines may be produced as the result of fusion between a non-immunoglobulin producing mouse myeloma cell line and spleen cells derived from a mouse immunized with purified hemoglobin receptor protein or a cell expressing antigens or epitopes of a bacterial hemoglobin receptor protein of the invention. The present invention also provides hybridoma cell lines that produce such antibodies, and can be injected into a living mouse to provide an ascites fluid from the mouse that is comprised of such antibodies. In a preferred embodiment. antibodies provided are raised against bacterial hemoglobin receptor protein isolated from bacteria of Neisseria species. In a particularly preferred embodiment, such antibodies are specific for the hemoglobin receptor protein isolated from *Neisseria meningitidis*.

It is a further object of the invention to provide immunologically-active epitopes of the bacterial hemoglobin receptor proteins of the invention. Chimeric antibodies immunologically reactive against the bacterial hemoglobin receptor proteins of the invention are also within the scope of this invention. In a preferred embodiment, antibodies and epitopes provided are raised against or derived from bacterial hemoglobin receptor protein isolated from bacteria of Neisseria species. In a particularly preferred embodiment, such antibodies and epitopes are specific for the hemoglobin receptor protein isolated from *Neisseria meningitidis*.

The present invention provides recombinant expression constructs comprising a nucleic acid encoding a bacterial hemoglobin receptor protein wherein the construct is capable of expressing the encoded hemoglobin receptor protein in cultures of cells transformed with the construct. Preferred embodiments of such constructs comprise the *N. meningitidis* hemoglobin receptor gene depicted in FIGS. 2A–2H (SEQ ID No.:1), such constructs being capable of expressing the bacterial hemoglobin receptor protein encoded therein in cells transformed with the construct.

The invention also provides cultures of cells, preferably bacterial cells, having been transformed with the recombinant expression constructs of the invention, such cultures being capable of and in fact expressing the bacterial hemoglobin receptor protein encoded in the transforming construct.

The present invention also includes within its scope protein preparations of prokaryotic cell membranes containing the bacterial hemoglobin receptor protein of the invention, derived from cultures of prokaryotic cells transformed with the recombinant expression constructs of the invention.

The invention also provides diagnostic reagents and methods for using such reagents for detecting the existence of an infection in a human, with bacteria of a Neisseria species. In preferred embodiments, such diagnostic reagents comprise antibodies that are immunologically reactive with a bacterial hemoglobin receptor protein. In a preferred embodiment, such antibodies are raised against a bacterial hemoglobin receptor protein isolated from bacteria of Neisseria species. In a particularly preferred embodiment, such antibodies are specific for the hemoglobin receptor protein isolated from *Neisseria meningitidis*.

In yet another embodiment of this aspect of the invention are provided diagnostic reagents and methods for using such reagents wherein said reagents are nucleic acid hybridization probes comprising a bacterial hemoglobin receptor gene. In a preferred embodiment, the bacterial hemoglobin receptor protein gene is isolated from bacteria of Neisseria species. In a particularly preferred embodiment, the hemoglobin receptor protein gene is isolated from *Neisseria meningitidis*. In particular examples of this embodiment of the invention, the nucleic acid probes comprise a specifically-hybridizing fragment of a 3.3 kilobase (kb) BamHI/HindIII fragment of *N. meningitidis* genomic DNA. In this embodiment, the nucleotide sequence comprises all or a specifically-hybridizing fragment of an open reading frame of 2376 nucleotides of *N.* meningitidis genomic DNA encoding 792 amino acids comprising the hemoglobin receptor gene. In this embodiment of the invention, the nucleotideA sequence of the *N. meningitidis* hemoglobin receptor gene is the sequence depicted in FIGS. 2A–2H (SEQ ID No: 1). It will be understood that the term "specifically-hybridizing" when used to describe a fragment of a nucleic acid encoding a bacterial hemoglobin receptor gene is intended to mean that nucleic acid hybridization of such a fragment is stable under high stringency conditions of hybridization and washing as the term "high stringency" would be understood by those having skill in the molecular biological arts.

Also provided by the invention are therapeutic agents and methods for using such agents for treating the an infection in a human with bacteria of a Neisseria species. In preferred embodiments, such agents comprise antibodies that are immunologically reactive with a bacterial hemoglobin receptor protein. In a preferred embodiment, such antibodies are raised against a bacterial hemoglobin receptor protein isolated from bacteria of Neisseria species. In a particularly preferred embodiment, such antibodies are specific for the hemoglobin receptor protein isolated from *Neisseria meningitidis*. Therapeutic agents provided in this aspect of the invention comprise such antibodies in a pharmaceutically-acceptable carrier, along with appropriate adjuvants and the like. In additional embodiments, such antibodies are covalently conjugated to a bactericidal or bacteriostatic agent effective against bacteria of Neisseria species, preferably *N. meningitidis*.

In yet another embodiment of this aspect of the invention are provided therapeutic reagents and methods for using such reagents wherein said reagents comprise recombinant expression constructs of the invention, or a homologue thereof that expresses the nucleic acid encoding a hemoglobin receptor in an antisense orientation. In a preferred embodiment, the bacterial hemoglobin receptor protein gene is isolated from bacteria of Neisseria species. In a particularly preferred embodiment, the hemoglobin receptor protein gene is isolated from *Neisseria meningitidis*. In particular examples of this embodiment of the invention, the nucleic acid probes comprise a specifically-hybridizing fragment of a 3.3 kilobase (kb) BamHI/HindIII fragment of *N. meningitidis* genomic DNA. In this embodiment, the nucleotide sequence comprises all or a specifically-hybridizing fragment of an open reading frame of 2376 nucleotides of *N. meningitidis* genomic DNA encoding 792 amino acids comprising the hemoglobin receptor gene.

The invention also provides a method for screening compounds for their ability to inhibit, facilitate or modulate the biochemical activity of a bacterial hemoglobin receptor protein of the invention, for use in the in vitro screening of novel agonist and antagonist compounds and novel bactericidal and bacteriostatic agents specific for the hemoglobin receptor protein. In preferred embodiments, cells transformed with a recombinant expression construct of the invention are contacted with such a compound, and the binding capacity of the compounds, as well as the effect of the compound on binding of other, known hemoglobin receptor agonists, such as hemoglobin and hemin, and antagonists is assayed. Additional preferred embodiments comprise quantitative analyses of such effects.

The present invention is also useful for the detection of bactericidal and/or bacteriostatic analogues, agonists or antagonists, recognized or unrecognized of a bacterial hemoglobin receptor protein, preferably derived from bacteria of Neisseria species, most preferably isolated from *N. meningitidis*, wherein such compounds are either naturally occurring or embodied as a drug.

The invention also provides vaccines for immunzig a human against infection with pathogenic bacteria of Neisseria species, the vaccines comprising the hemoglobin binding proteins of the invention or antigenic fragments thereof. In a preferred embodiment, the vaccines of the invention comprise cells expressing a hemoglobin receptor binding protein of the invention, or an antigenic fragment thereof, preferably wherein said cells are attenuated varieties of cells adapted for growth in humans. Examples of such attenuated varieties of cells include attenuated strains of *Salmonella typhi* and *Salmonella typhimurium*.

Specific preferred embodiments of the present invention will become evident from the following more detailed description of certain preferred embodiments and the claims.

DESCRIPTION OF THE DRAWINGS

The foregoing and other objects of the present invention, the various features thereof, as well as the invention itself may be more fully understood from the following description, when read together with the accompanying drawings in which:

FIGS. 2A–2H illustrates the nucleotide (SEQ ID No.:1) and deduced amino acid (SEQ ID No.:2) sequences of the *N. meningitidis* hemoglobin receptor protein encoded in a 3.3 kb BamHI/HindIII DNA fragment.

FIGS. 4A–4C presents an amino acid sequence comparison between portions of the *N. meningitidis* transferrin receptor Tbp1 (SEQ ID No. 3), the *N. meningitidis* lactoferrin receptor LbpA (SEQ ID No.: 4), and *N. meningitidis* hemoglobin receptor HmbR (SEQ ID No.:2).

DETAILED DESCRIPIION OF THIE PREFERRED EMBODIMENTS

Figure 1:
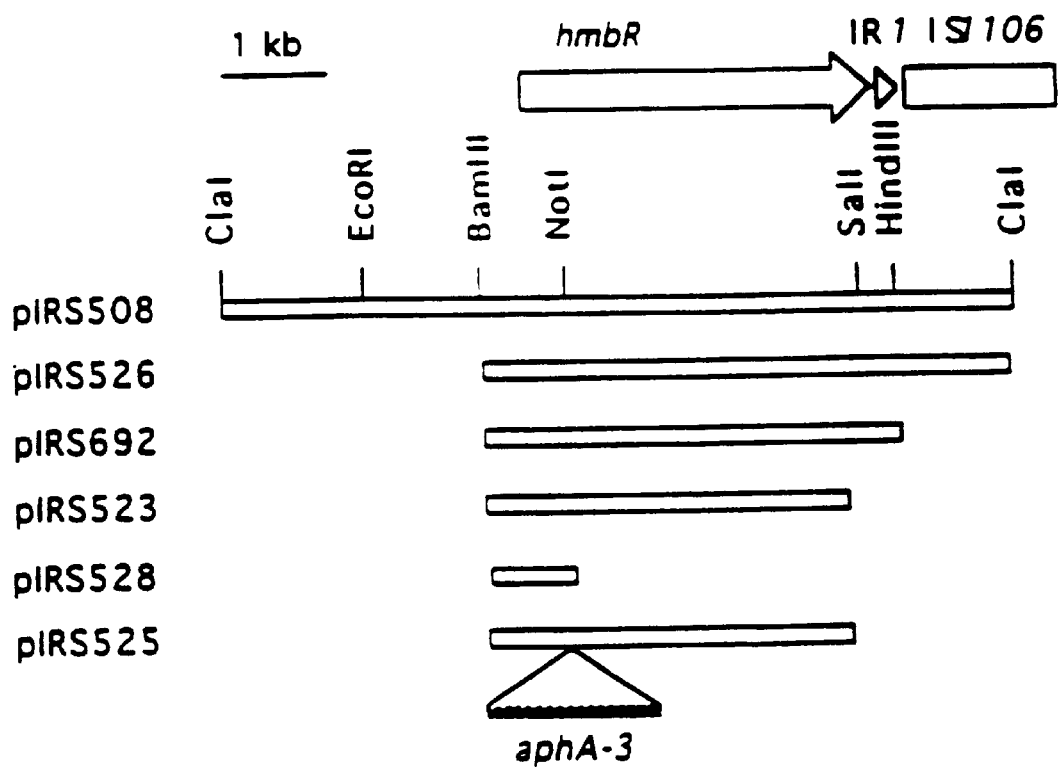
FIG. 1 is a schematic drawing of the restriction enzyme digestion map of a *N. meningitidis* cosmid clone and subclones thereof derived as described in Example 2.

The term "bacterial hemoglobin receptor" as used herein refers to bacterial proteins comprising the outer membrane of Gram negative bacteria, which specifically mediate transit of hemoglobin-derived hemin, as well as hemin from other sources, through the outer membrane of such bacteria and into the periplasmic space. The bacterial hemoglobin receptor proteins of the invention are characterized by, first, an amino acid sequence that is essentially the sequence depicted in FIGS. 2A–2H (SEQ ID No.:2). The bacterial hemoglobin receptor proteins of the invention are further characterized by having substantially the same biological activity as a protein having the amino acid sequence depicted in FIG. 2A–2H (SEQ ID No. :2). This definition is intended to encompass naturally-occurring variants and mutant proteins, as well as genetically engineered variants made by man.

Cloned, isolated and purified nucleic acid provided by the present invention may encode a bacterial hemoglobin receptor protein of any Neisseria species of origin, including, most preferably, *Neisseria meningitidis* and *Neisseria gonorhoeae* species.

The nucleic acid hybridization probes provided by the invention comprise DNA or RNA having all or a specifically-hybridizing fragment of the nucleotide sequence of the hemoglobin receptor protein as depicted in FIGS. 2A–2H (SEQ ID No.:1), or any portion thereof effective in nucleic acid hybridization. Mixtures of such nucleic acid hybridization probes are also within the scope of this embodiment of the invention. Nucleic acid probes as provided herein are useful for detecting the presence of a bacteria, inter alia, in a human as the result of an infection, in contaminated biological samples and specimens, in foodstuffs and water supplies, or in any substance that may come in to contact with the human. Specific hybridization will be understood to mean that the nucleic acid probes of the invention are capable of forming stable, specific hybridization to bacterially-derived DNA or RNA under conditions of high stringency, as the term "high stringency" would be understood by those with skill in the art (see, for example, Sambrook et al., 1989, *Molecular Cloning: A Laboratory Manual*, Cold Spring Harbor Laboratory Press, Cold Spring Harbor, N.Y. and Hames and Higgins, eds., 1985, *Nucleic Acid Hybridization*, IRL Press, Oxford, U.K.). Hybridization will be understood to be accomplished using well-established techniques, including but not limited to Southern blot hybridization, Northern blot hybridization, in situ hybridization and Southern hybridization to polymerase chain reaction product DNAs. The invention will thus be understood to provide oligonucleotides, specifically, pairs of oligonucleotides, for use as primers in support of in vitro amplification of bacterial hemoglobin receptor genes and mRNA transcripts.

The production of proteins such as bacterial hemoglobin receptor proteins from cloned genes by genetic engineering means is well known in this art. The discussion which follows is accordingly intended as an overview of this field, and is not intended to reflect the full state of the art. It will be understood from the following discussion that the hemoglobin receptor protein genes of this invention are particularly advantageous, since expression of such proteins by bacteria, including non-Neisseria species of bacteria, can complement certain auxotrophic mutants of said transformed bacteria otherwise unable to subsist absent supplementation of the growth media with iron (III).

DNA encoding a bacterial hemoglobin receptor protein can be prepared, in view of the instant disclosure, by chemical synthesis, by screening reverse transcripts of mRNA from appropriate cells, by screening genomic libraries from appropriate cells, or by combinations of these procedures, as illustrated below. Screening of mRNA or genomic DNA may be carried out with oligonucleotide probes generated from the nucleic acid sequence information from the bacterial hemoglobin receptor protein disclosed herein. Probes may be labeled with a detectable group such as a fluorescent group, a radioactive atom or a chemiluminescent group in accordance with know procedures and used in conventional hybridization assays, as described in greater detail in the Examples below. In the alternative, bacterial hemoglobin receptor protein-encoding nucleic acids may be obtained by use of the polymerase chain reaction (PCR) procedure, using appropriate pairs of PCR oligonucleotide primers corresponding to nucleic acid sequence information derived from a bacterial hemoglobin receptor protein as provided herein. See U.S. Pat. Nos. 4,683,195 to Mullis et al. and 4,683,202 to Mullis. In another alternative, such bacterial hemoglobin receptor protein-encoding nucleic acids may be isolated from auxotrophic cells transformed with a bacterial hemoglobin receptor protein gene, thereby relieved of the nutritional requirement for uncomplexed iron (III).

Any bacterial hemoglobin receptor protein of the invention may be synthesized in host cells transformed with a recombinant expression construct comprising a nucleic acid encoding the bacterial hemoglobin receptor protein. Such recombinant expression constructs can also be comprised of a vector that is a replicable DNA construct. Vectors are used herein either to amplify DNA encoding a bacterial hemoglobin receptor protein and/or to express DNA encoding a bacterial hemoglobin receptor protein. For the purposes of this invention, a recombinant expression construct is a replicable DNA construct in which a nucleic acid encoding a bacterial hemoglobin receptor protein is operably linked to suitable control sequences capable of effecting the expression of the bacterial hemoglobin receptor protein in a suitable host cell.

The need for such control sequences will vary depending upon the host cell selected and the transformation method chosen. Generally, bacterial control sequences include a transcriptional promoter, an optional operator sequence to control transcription, a sequence encoding suitable mRNA ribosomal binding sites (the Shine-Delgarno sequence), and sequences which control the termination of transcription and translation. Amplification vectors do not require expression control domains. All that is needed is the ability to replicate in a host, usually conferred by an origin of replication, and a selection gene to facilitate recognition of transformants. See, Sambrook et al., 1989, ibid.

Vectors useful for practicing the present invention include plasmids and virus-derived constructs, including phage and particularly bacteriophage, and integratable DNA fragments (i.e., fragments integratable into the host genome by homologous recombination). The vector replicates and functions independently of the host genome, or may, in some instances, integrate into the genome itself. Suitable vectors will contain replicon and control sequences which are derived from species compatible with the intended expression host. A preferred vector is pLAFR2 (see Riboli et al., 1991, *Microb. Pathogen.* 10: 393–403).

Transformed host cells are cells which have been transformed or transfected with recombinant expression constructs made using recombinant DNA techniques and comprising nucleic acid encoding a bacterial hemoglobin receptor protein. Preferred host cells are cells of Neisseria species, particularly *N. meningitidis, Salmonella typhi* and *Salmonella typhimurium*, and *Escherichia coli* auxotrophic mutant cells (hemA aroB). Transformed host cells may express the bacterial hemoglobin receptor protein, but host cells transformed for purposes of cloning or amplifying nucleic acid hybridization probe DNA need not express the receptor protein. When expressed, the bacterial hemoglobin receptor protein of the invention will typically be located in the host cell outer membrane. See, Sambrook et al., ibid.

Cultures of bacterial cells, particularly cells of Neisseria species, and certain *E. coli* mutants, are a desirable host for recombinant bacterial hemoglobin receptor protein synthesis. In principal, any bacterial cell auxotrophic for uncomplexed iron (III) is useful for selectively growing bacterial hemoglobin receptor protein-transformed cells. However, for this purpose, well-haracterized auxotrophs, such as *E. coli* hemA aroB mutants are preferred.

The invention provides homogeneous compositions of a bacterial hemoglobin receptor protein produced by transformed cells as provided herein. Each such homogeneous composition is intended to be comprised of a bacterial hemoglobin receptor protein that comprises at least 90% of the protein in such a homogenous composition. The invention also provides membrane preparations from cells expressing a bacterial hemoglobin receptor protein as the result of transformation with a recombinant expression construct of the invention, as described herein.

Bacterial hemoglobin receptor proteins, peptide fragments thereof and membranes derived from cells expressing such proteins in accordance with the present invention may be used for the production of vaccines effective against bacterial infections in a human, with pathogenic microorganisms expressing such bacterial hemoglobin receptor proteins. Such vaccines preferably would be effective in raising an immunological response against bacteria of Neisseria species, most preferably *N. meningitidis* and *N. gonorhoeae*. Preparation of vaccines which contain polypeptide sequences as active ingredients is well understood in the art. Typically, such vaccines are prepared as injectables, either as liquid solutions or suspensions. However, solid forms suitable for solution in, or suspension in, liquid prior to injection may also be prepared. The preparation may also be emulsified. The active immunogenic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, or adjuvants which enhance the effectiveness of the vaccine. The vaccines are conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkalene glycols or triglycerides; such suppositories may be formed from mixtures containing the active ingredient in the range of 0.5% to 10%, preferably 1 to 2%. Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders and contain 10% to 95% of active ingredient, preferably 25 to 70%.

The polypeptide may be formulated into the vaccine as neutral or salt forms. Pharmaceutically acceptable salts include the acid additional salts (formed with the free amino groups of the peptide) and which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

In another embodiment, such vaccines are provided wherein the bacterial hemoglobin receptor proteins or peptide fragments thereof are present in the intact cell membranes of cells expressing such proteins in accordance with the present invention. In preferred embodiments, cells useful in these embodiments include attenuated varieties of cells adapted to growth in humans. Preferred examples of such attenuated cells include attenutated varieties of *Salmonella typhi* and *Salmonella typhimurium*. It will be understood that these embodiments of the vaccines of the invention encompass so-called "live" attenuated cell preparations as well as heat- or chemically-inactivated cell preparations.

The vaccines of the invention are administered in a manner compatible with the dosage formulation, and in such amount as will be therapeutically effective and immunogenic. The quantity to be administered depends on the subject to be treated, capacity of the subject's immune system to synthesize antibodies, and the degree of protection desired. Precise amounts of active ingredient required to be administered depend on the judgment of the practitioner and are peculiar to each individual. However, suitable dosage ranges are of the order of several hundred micrograms active ingredient per individual. Suitable regimes for initial administration and booster shots are also variable, but are typified by an initial administration followed in one or two week intervals by a subsequent injection or other administration.

The recombinant expression constructs of the present invention are useful in molecular biology to transform bacterial cells which do not ordinarily express a hemoglobin receptor protein to thereafter express this receptor. Such cells are useful, inter alia, as intermediates for making cell membrane preparations useful for receptor binding activity assays, vaccine production, and the like, and in certain embodiments may themselves be used, inter alia, as vaccines or components of vaccines, as described above. The recombinant expression constructs of the present invention thus provide a method for screening potentially useful bactericidal and bacteriostatic drugs at advantageously lower cost than conventional screening protocols. While not completely eliminating the need for ultimate in vivo activity and toxicology assays, the constructs and cultures of the invention provide an important first screening step for the vast number of potentially useful bactericidal and bacteriostatic drugs synthesized, discovered or extracted from natural sources each year. In addition, such bactericidal or bacteriostatic drugs would be selected to utilize a nutritional pathway associated with infectious virulence in these types of bacteria, as disclosed in more detail below, thus selectively targeting bacteria associated with the development of serious infections in vivo.

Also, the invention provides both functional bacterial hemoglobin receptor proteins, membranes comprising such proteins, cells expressing such proteins, and the amino acid sequences of such proteins. This invention thereby provides sufficient structural and functional activity information to enable rational drug design of novel therapeutically-active antibacterial drugs using currently-available techniques (see Walters, "Computer-Assisted Modeling of Drugs", in Klegerman & Groves, eds., 1993, *Pharmaceutical Biotechnology*, Interpharm Press: Buffalo Grove, Ill., pp. 165–174).

Nucleic acids and oligonucleotides of the present invention are useful as diagnostic tools for detecting the existence of a bacterial infection in a human, caused by a hemoglobin receptor protein-expressing pathological organism of Neisseria species. Such diagnostic reagents comprise nucleic acid hybridization probes of the invention and encompass paired oligonucleotide PCR primers, as described above. Methods provided by the invention include blot hybridization, in situ hybridization and in vitro amplification techniques for detecting the presence of pathogenic bacteria in a biological sample. Appropriate biological samples advantageously screened using the methods described herein include plasma, serum, lymph, cerebrospinal fluid, seminal fluid, mucosal tissue samples, biopsy samples, and other potential sites of bacterial infection. It is also envisioned that the methods of the invention may be used to screen water, foodstuffs, pharmaceuticals, and other potential sources of infection.

The invention also provides antibodies that are immunologically reactive to a bacterial hemoglobin receptor protein or epitopes thereof provided by the invention. The antibodies provided by the invention may be raised, using methods well known in the art, in animals by inoculation with cells that express a bacterial hemoglobin receptor protein or epitopes thereof. cell membranes from such cells, whether crude membrane preparations or membranes purified using methods well known in the art, or purified preparations of proteins, including fusion proteins, particularly fusion proteins comprising epitopes of a bacterial hemoglobin receptor protein of the invention fused to heterologous proteins and expressed using genetic engineering means in bacterial, yeast or eukaryotic cells, said proteins being isolated from such cells to varying degrees of homogeneity using conventional biochemical means. Synthetic peptides made using established synthetic means in vitro and optionally conjugated with heterologous sequences of amino acids, are also encompassed in these methods to produce the antibodies of the invention. Animals that are used for such inoculations include individuals from species comprising cows, sheep, pigs, mice, rats, rabbits, hamsters, goats and primates. Preferred animals for inoculation are rodents (including mice, rats, hamsters) and rabbits. The most preferred animal is the mouse.

Cells that can be used for such inoculations, or for any of the other means used in the invention, include any cell that naturally expresses a bacterial hemoglobin receptor protein as provided by the invention, or any cell or cell line that expresses a bacterial hemoglobin receptor protein of the invention, or any epitope thereof, as a result of molecular or genetic engineering, or that has been treated to increase the expression of an endogenous or heterologous bacterial hemoglobin receptor protein by physical, biochemical or genetic means. Preferred cells are *E. coli* auxotrophic mutant hemA aroB cells transformed with a recombinant expression construct of the invention and grown in media supplemented with hemin or hemoglobin as the sole iron (III) source, and cells of Neisseria species.

The present invention also provides monoclonal antibodies that are immunologically reactive with an epitope of a bacterial hemoglobin receptor protein of the invention, or fragment thereof, present on the surface of such cells, preferably *E. coli* cells. Such antibodies are made using methods and techniques well known to those of skill in the art. Monoclonal antibodies provided by the present invention are produced by hybridoma cell lines, that are also provided by the invention and that are made by methods well known in the art (see Harlow and Lane, 1988, *Antibodies: A Laboratory Manual*, Cold Spring Harbor Laboratory Press, Cold Spring Harbor, N.Y.).

Hybridoma cell lines are made by fusing individual cells of a mycloma cell line with spleen cells derived from animals immunized with a homogeneous preparation of a bacterial hemoglobin receptor protein, membranes comprised thereof, cells expressing such protein, or epitopes of a bacterial hemoglobin receptor protein, used per se or comprising a heterologous or fusion protein construct, as described above. The myeloma cell lines used in the invention include lines derived from myelomas of mice, rats, hamsters, primates and humans. Preferred myeloma cell lines are from mouse, and the most preferred mouse myeloma cell line is P3X63-Ag8.653. Preferred animals from whom spleens are obtained after immunization are rats, mice and hamsters, preferably mice, most preferably Balb/c mice. Spleen cells and myeloma cells are fused using a number of methods well known in the art, including but not limited to incubation with inactivated Sendai virus and incubation in the presence of polyethylene glycol (PEG). The most preferred method for cell fusion is incubation in the presence of a solution of 45% (w/v) PEG-1450. Monoclonal antibodies produced by hybridoma cell lines can be harvested from cell culture supernatant fluids from in vitro cell growth; alternatively, hybridoma cells can be injected subcutaneously and/or into the peritoneal cavity of an animal, most preferably a mouse, and the monoclonal antibodies obtained from blood and/or ascites fluid.

Monoclonal antibodies provided by the present invention are also produced by recombinant genetic methods well known to those of skill in the art, and the present invention encompasses antibodies made by such methods that are immunologically reactive with an epitope of a bacterial hemoglobin receptor protein of the invention. The present invention also encompasses fragments, including but not limited to F(ab) and F(ab)'$_2$ fragments, of such antibody. Fragments are produced by any number of methods, including but not limited to proteolytic cleavage, chemical synthesis or preparation of such fragments by means of genetic engineering technology. The present invention also encompasses single-hain antibodies that are immunologically reactive with an epitope of a bacterial hemoglobin receptor protein, made by methods known to those of skill in the art.

The antibodies and fragments used herein can be labeled preferably with radioactive labels, by a variety of techniques. For example, the biologically active molecules can be labeled with a radionucleotide via conjugation with the cyclic anhydride of diethylenetriamine penta-acetic acid (DPTA) or bromoacetyl aminobenzyl ethylamine diamine tetra-acidic acid (BABE). See Hnatowich et al. (1983, *Science* 220: 613–615) and Meares et al. (1984, *Anal. Biochem.* 142: 68–78, both references incorporated by reference) for further description of labeling techniques.

The present invention also encompasses an epitope of a bacterial hemoglobin receptor protein of the invention, comprised of sequences and/or a conformation of sequences present in the receptor molecule. This epitope may be naturally occurring, or may be the result of proteolytic cleavage of a receptor molecule and isolation of an epitope-containing peptide or may be obtained by synthesis of an epitope-containing peptide using methods well known to those skilled in the art. The present invention also encompasses epitope peptides produced as a result of genetic engineering technology and synthesized by genetically engineered prokaryotic or eukaryotic cells.

The invention also includes chimeric antibodies, comprised of light chain and heavy chain peptides immunologically reactive to a bacterial hemoglobin receptor protein-derived epitope.

The chimeric antibodies embodied in the present invention include those that are derived from naturally occurring antibodies as well as chimeric antibodies made by means of genetic engineering technology well known to those of skill in the art.

Also provided by the present invention are diagnostic and therapeutic methods of detecting and treating an infection in a human, by pathogenic organisms expressing a bacterial hemoglobin receptor protein. Diagnostic reagents for use in such methods include the antibodies, most preferably monoclonal antibodies, of the invention. Such antibodies are used in conventional immunological techniques, including but not limited to enzyme-linked immunosorbent assay (ELISA), radioimmune assay (RIA), Western blot assay, immunological titration assays, immunological diffusion assays (such as the Ouchterlony assay), and others known to those of skill in the art. Also provided are epitopes derived from a bacterial hemoglobin receptor protein of the invention and immunologically cross-reactive to said antibodies, for use in any of the immunological techniques described herein.

Additional diagnostic assays include nucleic acid hybridization assays, using the nucleic acids of the invention or specifically-hybridizing fragments thereof, for sensitive detection of bacterial genomic DNA and/or mRNA. Such assays include various blot assays, such as Southern blots, Northern blots, dot blots, slot blots and the like, as well as in vitro amplification assays, such as the polymerase chain reaction assay (PCR), reverse transcriptase-polymerase chain reaction assay (RT-PCR), ligase chain reaction assay (LCR), and others known to those skilled in the art. Specific restriction endonuclease digestion of diagnostic fragments detected using any of the methods of the invention, analogous to restriction fragment linked polymorphism assays (RFLP) are also within the scope of this invention.

The invention also provides therapeutic methods and reagents for use in treating infections in a human, cause by a microorganism expressing a bacterial hemoglobin receptor protein of the invention, most preferably a bacteria of Neisseria species. Therapeutic reagents for use in such methods include the antibodies, most preferably monoclonal antibodies, of the invention, either per se or conjugated to bactericidal or bacteriostatic drugs or other antibiotic compounds effective against the infectious microorganism. In such embodiments, the antibodies of the invention comprise pharmaceutical compositions, additionally comprising appropriate pharmaceutically-acceptable carriers and adjuvants or other ancillary components where necessary. Suitable carriers are, for example, water, saline, dextrose, glycerol, ethanol, or the like and combinations thereof. In addition, if desired, the pharmaceutical formulation may contain minor amounts of auxiliary substances such as wetting or emulsifying agents, pH buffering agents, or other compounds which enhance the effectiveness of the antibody. In these embodiments, it will be understood that the therapeutic agents of the invention serve to target the infectious bacteria, either by immunologically "tagging" the bacteria with an antibody of the invention for recognition by cytotoxic cells of a human's immune system, or by specifically delivering an antimicrobial drug to the infectious microorganism via the bacterial hemoglobin receptor protein.

Additional therapeutic reagents include the nucleic acids of the invention or fragments thereof, specifically antisense embodiments of such nucleic acids. Such antisense nucleic acids may be used themselves or embodied in a recombinant expression construct specific for antisense expression, wherein said construct is genetically engineered to co-opt a portion of the genome of a bacterial virus, preferably a bacteriophage, infectious for the bacterial pathogen responsible for the infection. In these embodiments, introduction of the antisense nucleic acids of the invention into the bacterial cell inhibits, attenuates or abolishes expression of the bacterial hemoglobin receptor, thereby reducing the virulence of the bacterial infection and enabling more effective antibacterial interventions. In additional embodiments, bacteriophage are provided bearing "knockout" copies of a bacterial hemoglobin receptor gene, whereby the phage achieves genetic mutation of the endogenous hemoglobin receptor gene in the infectious bacteria via, for example, homologous recombination of the exogenous knockout copy of the bacterial hemoglobin receptor gene with the endogenous hemoglobin receptor gene in the infectious microorganism.

The Examples which follow are illustrative of specific embodiments of the invention, and various uses thereof. They set forth for explanatory purposes only, and are not to be taken as limiting the invention.

EXAMPLE 1

Plasmids, bacteria, and media

Plasmids and bacteria used herein are listed on Table 1. *E. coli* strains were routinely grown in Luria-Bertani (LB) broth supplemented with 5-aminolevulinic acid and 50 mg/L hemin chloride as necessary. *N. meningitidis* 8013 is a serogroup C clinical isolate (Nassif et al., 1993, *Mol. Microbiol.* 8: 719–725). The meningococci were routinely grown on GCB agar (Difco) supplemented as described by Kellogg et al. (1963, *J. Bacteriol* 85: 1274–1279), and incubated at 37° C. under a 5 % $CO_2$ atmosphere. Transformation of meningococci was performed as described by Nassif et al. (1992, *Mol. Microbiol.* 6: 591–597). When necessary, the following antibiotics were used with *E. coli*: rifampicin, 100 mg/L; tetracycline, 15 mg/L; kanamycin, 30 mg/L; chloramphenicol, 20 mg/L; carbenicillin, 100 mg/L. For Neisseriae, kanamycin at 100 mg/L was used when needed.

EXAMPLE 2

Auxotroph Complementation Cloning of a Hemoglobin Receptor Gene from *Neisseria meningtidis*

In order to identify *N. meningitidis* outer membrane receptor(s) involved in the uptake of hemin and/or hemoglobin iron, an auxotroph complementation cloning strategy was used, similar to the approach previously taken to identify the *Y. enterocolitica* and *V. cholerae* hemin

TABLE 1

Bacterial Strains and Plasmids

| STRAIN | GENOTYPE |
|---|---|
| *E. coli* K12 | |
| EB53 | hemA, aroB, rpoB |
| KP1041 | MC4100tonB::$Km^r$ |
| H1388 | exbB::Tn10 Δlac pro |
| TSM348 | endA, hsdR, pro, supF, pRK2013::Tn9 |

TABLE 1-continued

Bacterial Strains and Plasmids

| STRAIN | GENOTYPE |
| --- | --- |
| IR754 | EB53, tonB::Km$^r$ |
| IR736 | EB53, exbB::Tn10 |
| DH5α | recA, gyrB |
| *N. meningitidis* | |
| MC8013 | clone 6, wild type |
| MChmbR | hmbR::aphA-3 |
| PLASMIDS | |
| pSUSK | pA15 replicon, chloramphenicol$^r$ |
| pHEM22 | pLAFR2, hemoglobin-utilizing cosmid |
| pHEM44 | pLAFR2, hemin-utilizing cosmid |
| pIRS508 | 6 kb ClaI, pSUSK |
| pIRS523 | 3 kb BamHI/SalI, pUC19 |
| pIRS525 | 1.2 kb aphA-3, in NotI site of pIRS523 |
| pIRS527 | 4 kb BamHI/ClaI, pBluescript |
| pIRS528 | 0.7 kb NotI/BamHI, pBluescript |
| pIRS692 | 3.3 kb BamHI/HindIII, SU(SK) | receptors (see Stojiljkovic and Hantke, 1992, *EMBO J.* 11: 4359–4367; Henderson and Payne, 1994, *J. Bacteriol.* 176: 3269–3277). This strategy is based on the fact that the outer membrane of Gram-negative bacteria is impermeable to hemin (McConville and Charles, 1979, *J. Microbiol.* 113: 165–168) and therefore *E. coli* porphyrin biosynthesis mutants cannot grow on exogenously supplied hemin. If provided with the *N. meningitidis* outer membrane hemin receptor gene, the *E. coli* porphyrin mutant would be able to use exogenously supplied hemin as its porphyrin source.

A cosmid bank of *N. meningitidis* 8013 clone 6 DNA was prepared using conventional cosmid cloning methodologies (Sambrook et al., 1989, ibid.). *N. meningitidis* bacterial DNA was partially digested by MboI, size fractionated on sucrose gradients and cloned into the BamHI site of the cosmid vector pLAFR2 (Riboli et al., 1991, *Microb. Pathogen.* 10: 393–403). This cosmid bank was mobilized into the *E. coli* hemA aroB Rif$^r$ recipient strain by triparental matings using a conjugal plasmid pRK2013::Tn9. The mating mixture was plated onselective plates containing hemin chloride (50 mg/L), 0.1 mM 2,2'-dypyridil and rifampicin (100 mg/L). Several clones growing on exogenously supplied hemin were isolated after an overnight incubation.

The hemin utilization phenotype of these transformants was tested by re-introduction of the cosmids into naive *E. coli* hemA aroB cells and by monitoring the growth on hemin-supplemented plates. The ability of *E. coli* strains to utilize heme or hemoglobin as the sole iron source was tested as previously described (Stojiljkovic and Hantke, 1992, ibid.). Cells were grown on LB agar supplemented with 50 μM deferoxamine mesylate (an iron chelating agent, obtained from Sigma Chemical Co., St. Louis, Mo.). Filter discs (¼ inches, Schleichner & Schuell, Inc., Keene, N.H.) impregnated with the test compounds (20 μL of 5 mg/ml stock solutions unless otherwise stated) were placed on these plates. After overnight growth at 37° C. with 5% $CO_2$, zones of growth around the discs were monitored. The iron-bound proteins tested in this assay (all obtained from Sigma Chemical Co.) were hemoglobin from human, baboon, bovine and mouse sources, bovine hemin, human lactoferrin (90% iron saturated), and human transferrin (90% iron saturated, obtained from Boehringer Mannheim Biochemicals, Indianapolis, Ind.). A total of six hemin utilization positive cosmids were obtained using this protocol. Results using such assays are shown in Table II.

TABLE II

| STRAIN | φ-TYPE | HEMIN IRON | POR-PHYRIN | Hb IRON |
| --- | --- | --- | --- | --- |
| *N. meningitidis* | | | | |
| MC8013 | wild type | +++ | N.T. | +++ |
| MChmbR | Hb$^R$ mutant | +++ | N.T. | − |
| *E.coli* | | | | |
| EB53 | iron utilization | − | − | − |
| EB53 (pIRS508) | tonB+,exbB+,hmbR+ | +++ | +++ | + |
| IR754(pIRS508) | tonB−,exbB+,hmbR+ | − | − | − |
| IR736(pIRS508) | tonB+,exbB−,hmbR+ | − | − | − |

N.T.-not tested. Use of hemin/hemoglobin as a porphyrin source was tested by scoring for growth of strains around hemin (5 mg/mL) or hemoglobin (for *E. coli*, 10 mg/mL; for *N. meningitidis*, 5 mg/mL) discs on LB plates. The use of the hemin/hemoglobin as an iron source was tested similarly except NBD plates supplemented with 50 μL of 5 g/L delta-aminolevulinic acid were used (GCB plates supplemented with the 50 μM Desferal in the case of *N. meningitidis*).

−: indicates no growth; +:less then 100 mm of growth zone around the disc: +++:±15 mm of growth zone around the disc.

EXAMPLE 3

Restriction Enzyme Digestion Mapping of Hemin Utilization Positive Cosmids

Cosmid DNA from six hemin-utilization positive cosmids obtained as described in Example 2 were digested with ClaI, and the resulting fragments were cloned into ClaI-digested pSU(SK) vector (obtained from Stratagene, LaJolla, Calif.). One subclone, containing a 6 kb ClaI fragment from cosmid cos22 (the resultant plasmid was designated pIRS508), was determined to allow utilization of hemin and hemoglobin by *E. coli* hemA aroB assayed as described in Example 2. Another such clone, containing an 11 kb ClaI fragment from cos44 was also determined to allow hemin utilization in these auxotrophic mutant cells. Restriction analysis and Southern hybridization indicated that the DNA fragments originating from cos22 and cos44 are unrelated.

The deduced restriction enzyme digestion map of cosmid clone pIRS508 is shown in FIG. 1. Plasmid pIRS508 enabled *E. coli* hemA aroB to use both hemin and bovine hemoglobin as iron sources although growth on hemoglobin was somewhat weaker than on hemin (Table 2). Further subcloning localized the hemin/hemoglobin utilization locus to the BamHI/HindIII fragment of the insert. In addition to sequences encoding the hemoglobin receptor gene (designated hmbR), sequences for a Neisseria insertion element (IS1106) and a portion of a Neisseria small repetitive element (IR1) are also represented in the Figure.

EXAMPLE 4

Nucleotide Sequence Analysis of a Cosmid Clone Encoding a Neisseria Hemoglobin Receptor Gene The nucleotide sequence of the 3.3 kb BamHI-HindIII DNA fragment carrying the hmbR gene and its promoter region was determined using the dideoxy chain termination method using a Sequenase 2.0 kit (obtained from U.S. Biochemicals, Cleveland, Ohio) and analyzed using a Bio-Rad electrophoresis system, an AutoRead kit (obtained from Pharmacia, Uppsala, Sweden) and an ALF-370 automatic sequenator (Pharmacia). Plasmid subclones for sequencing were produced by a nested deletion approach using Erase-a-Base kit (obtained from Promega Biotech, Madison, Wis.) using different restriction sites in the hmbR gene. The nucleotide and predicted amino acid sequences of the hmbR gene are shown in FIGS. 2A–2H.

An open reading frame (ORF) encoding the *N. meningitidis* hemoglobin receptor protein begins at position 470 of the sequence and encodes a protein having an amino acid sequence of 792 amino acids, with a calculated molecular weight of 85.5 kDa. A Shine-Delgarno sequence (SD) is found at position 460. The HmbR receptor protein contains a signal peptidase I recognition sequence at residues 22 to 24 of the protein (underlined), consistent with the fact that it is an outer membrane protein.

A typical Fur binding nucleotide sequence (designated "Fur box") was found in the promoter region of the hmbR gene (FIGS. 2A–2H). Like hemin utilization in Yersiniae and Virio, hemin and hemoglobin utilization in Neisseria are known to be iron-inducible phenotypes (West and Sparling, 1985, *Infect. Immun.* 47: 388–394; Dyer et al., 1987, *Infect. Immun.* 55: 2171–2175). In Gram-negative bacteria, conditional expression of many iron utilization genes is regulated by the Fur repressor, which recognizes a 19 bp imperfect dyad repeat (Fur-box) in the promoter regions of Fur-repressed genes. Recently, a genetic screen (FURTA) for the identification of Fur-regulated genes from different Gram-negative bacteria was described (Stojiljkovic et al., 1994, *J. Mol. Biol.* 236: 531–545), and this assay was used to test whether hmbR expression was controlled in this way. Briefly, a plasmid carrying a Fur-box sequence is transformed into an *E. coli* strain (H1717) which possesses a Fur-regulated lac fusion in the chromosome. Expression of this Fur-regulated lac fusion is normally repressed. Introduction of a multicopy Fur-box sequence on the plasmid titrates the available Fur repressor thus allowing expression of the Fur-regulated lac fusion (this phenotype is termed FURTA positive). Using this screen, the smallest insert fragment from cosmid pIRS508 that produced a FURTA positive result was a 0.7 kb BamHI-NotI DNA fragment carried on plasmid pIRS528 (see FIG. 1). This result indicated that the 0.7 kb BamHI-NotI fragment carries a Fur-box and that gene expression from the hmbR promoter is controlled by a Fur-type operon.

Figure 3:
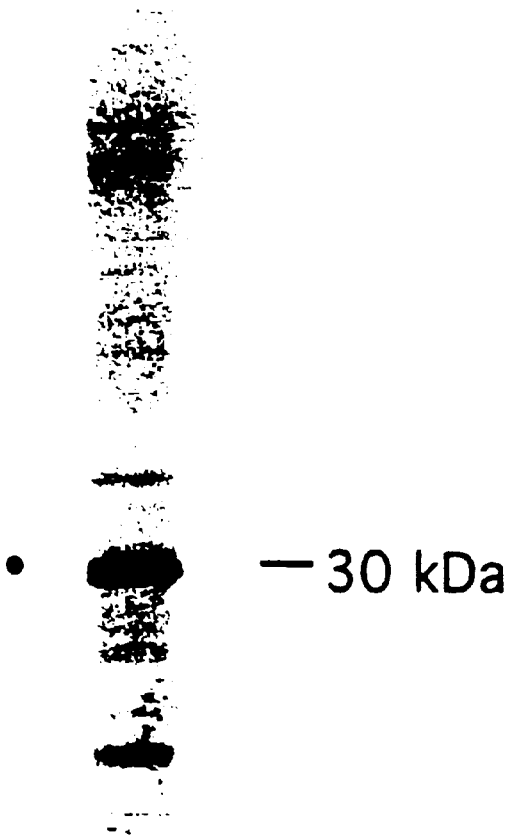
FIG. 3 presents a photograph of a stained SDS/ 10% PAGE electrophoresis gel showing the results of in vitro expression of the *N. meningitidis* hemoglobin receptor gene product as an approximately 90 kilodalton protein, and β-lactamase protein having a molecular weight of about 30.0 kilodaltons used as a molecular weight marker.

The *N. meningitidis* hemoglobin receptor protein was expressed in vitro using an *E. coli* S30 extract system from Promega Biotech (Madison, Wis.). The 3.3 kb BamHI-HindIII fragment, expressed in vitro, encoded a 90 kDa protein which corresponds in size to the predicted molecular weight of the unprocessed HmbR receptor. SDS/10% PAGE analysis showing the observed $M_r$ of 90K is shown in FIG. 3.

Immediately downstream of the hmbR gene (at positions 2955 to 3000 bp in FIGS. 2A–2H) was found a short nucleotide sequence that is 99% identical to the flanking sequence of the PIII gene of *N. gonorrhoeae* (Gotschlich et al., 1987, *J. Exp. Med.* 165: 471–482). The first 26 bp of this sequence represents one half of the inverted repeat (IRI) of the *N. gonorrhoeae* small repetitive element. This element is found in approximately 20 copies in both *N. gonorrhoeae* and *N. meningitidis* (Correia et al., 1988, *J. Biol. Chem.* 263: 12194–12198). The analysis of the nucleotide sequence from position 3027 to the ClaI (3984) restriction site (only the nucleotide sequence from BamHI (1) to HindIII (3370) is shown in FIGS. 2A–2H ) indicated the presence of an IS1106 element (Knight et at., 1992, *Mol. Microbiol.* 6: 1565–1573). Interestingly, no nucleotide sequence similar to the IS1106 inverted repeat was found between the IR1 element and the beginning of the homology to IS1106.

These results were consistent with the cloning and identification of a novel hemoglobin receptor protein gene from *N. meningitidis*, embodied in a 3.3 kb BamHI/HindIII fragment of *N. meningitidis* genomic DNA.

EXAMPLE 5

Amino Acid Sequence Comparison of the *N. meningitidis* Hemoglobin Receptor Protein and Neisseria Lactoferrin and Transferrin Receptor Proteins A comparison of the transferrin (Thp1; Legrain et al., 1993, *Gene* 130: 81–90), lactoferrin (LbpA; Pettersson et al., 1993, *Infect. Immun.* 61: 4724–4733, and 1994, *J. Bacteriol.* 176: 1764–1766) and hemoglobin receptors (HmbR) from *N. meningitidis* is shown in FIGS. 4A–4C. The comparison was done with the CLASTAL program from the PC/GENE program package (Intelligenetics, Palo Alto, Calif.). Only the amino-terminal and carboxyl terminal segments of the proteins are shown. An asterisk indicates identity and a point indicates similarity at the amino acid level. Lactofernin and transfernin receptors were found to share 44.4% identity in amino acid sequence. In contrast, homology between these proteins and the hemoglobin receptor disclosed herein was found to be significantly weaker (22% amino acid sequence identity with lactoferrin and 21% with transferrin receptor).

EXAMPLE 6

TonB/ExbBD-Dependence of Hemin Transport by the *N. meningitidis* Hemoglobin Receptor It was known that the transport of iron-containing siderophores, some colicins and vitamin B12 across the outer membrane of *E. coli* depends on three cytoplasmic membrane proteins: TonB, ExbB and ExbD (Postle, 1990, *Mol. Microbiol.* 133: 891–898; Braun and Hantke, 1991, in Winkelmann, (ed.), *Handbook of Microbial Iron Chelates*, CRC Press. Boca Raton, Fla., pp. 107–138). In Yersinia and Hemophilus, hemin uptake was shown to be a TonB-dependent process (Stojiljkovic and Hantke, 1992, ibid.; Jarosik et al., 1994, *Infect. Immun.* 62: 2470–2477). Through direct interaction between the outer membrane receptors and the TonB cytoplasmic machinery, the substrate bound to the receptor is internalized into the periplasm (Heller et al., 1988, *Gene* 64: 147–153; Schoffler and Braun, 1989, *Molec. Gen. Genet.* 217: 378–383). This direct interaction has been associated with a particular amino acid sequence in membrane proteins associated with the TonB machinery.

All TonB-dependent receptors in Gram-negative bacteria contain several regions of high homology in their primnary structures (Lundrigan and Kadner, 1986, *J. Biol. Chem.* 261: 10797–10801). In the amino acid sequence comparison described in Example 5, putative TonB-boxes of all three proteins are underlined. The carboxyl terminal end of the HmbR receptor contains the highly conserved terminal phenylalanine and −11 arginine residues thought to be part of an outer membrane localization signal (Struyve et al., 1991, *J. Mol. Biol.* 218: 141–148; Koebnik, 1993, *Trends Microbiol.* 1: 201). At residue 6 of the mature HmbR protein, an amino acid sequence - ETTPVKA(SEQ.ID.No.5) - is similar in sequence to the so called TonB-boxes of several Gram-negative receptors (Heller et al., 1988, ibid.). Interestingly, the putative TonB-box of HmbR has more homology to the TonB-box of the *N. gonorrhoeae* transferrin receptor (Cornelissen et al., 1992, *J. Bacteriol.* 174: 5788–5797) than to the TonB-boxes of *E. coli* siderophore receptors. When the sequence of the HmbR receptor was compared with other TonB-dependent receptors, the highest similarity was found with *Y. enterocolitica* HemR receptor although the similarity was not as high as to the Neisseria receptors.

In order to prove the TonB-dependent nature of the *N. meningitidis* hemoglobin receptor, hmbR was introduced into exbB and tonB mutants of *E. coli* EB53, and the ability of the strains to utilize hemin and hemoglobin as porphyrin and iron sources was assessed. In these assays, both mutants of *E. coli* EB53 were unable to use hemin either as a porphyrin source or as an iron source in the presence of a functional hmbR (Table II). The usage of hemoglobin as an iron source was also affected (Table II). These results are consistent with the notion that the hmbR gene product, the *N. meningitidis* hemoglobin receptor protein of the invention, is TonB-dependent, since expression of this gene in TonB wild type *E. coli* supported the use of hemin and hemoglobin as sole iron source in the experiments disclosed in Example 2.

EXAMPLE 7

Functional Demonstration that the hmbR Gene Product is the Hemoglobin Receptor Protein in *N. meningilidis*

Figure 5:
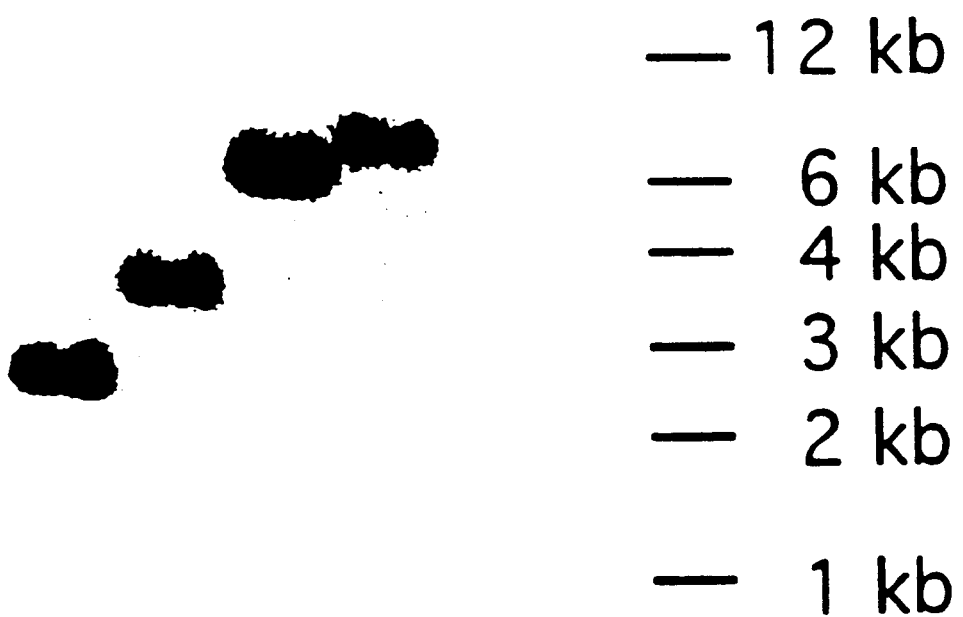
FIG. 5 illustrates Southern hybridization analysis of chromosomal DNA from *N. meningitidis* 8013 and the MC8013hmbR mutant using a BamHI-SalI fragment of the hmb gene as probe labeled using a DIG nonradioactive DNA labelling and detection kit (Boehringer Mannheim Biochemicals, Indianapolis, Ind.). Lane 1 contains DNA from *N. meningitidis* strain MC8013, digested with ClaI; lane 2 is MC8031hmbR DNA digested with ClaI; lane 3, is MC8013 DNA digested with BamHI and SalI; and lane 4 is MC8013hmbR DNA digested with BamHI and SalI.

As shown in the data presented in Table II, hmbR mediated both hemin and hemoglobin utilization when expressed in *E. coli*, but hemoglobin utilization was less vigorous than hemin utilization. To determine if the HmbR receptor has the same specificity in *N. meningitidis*, hmbR was inactivated with a 1.2 kb kanamycin cassette (aphA-3; Nassif et al., 1991, ibid.) and transformed into wild-type *N. meningitidis* 8013 clone 6 cells. The inactivation of the chromosomal hmbR copy of the Km-resistant taansformants was confirmed by Southern hybridization, as shown in FIG. 5. As can be seen from FIG. 5, wild-type *N. meningitidis* genomic DNA contains only one copy of the hmbR gene (lanes 1 and 3). In the Km$^r$ transformants, the size of the DNA fragments containing the wild-type gene has increased by 1.2 kb, which is the size of the Kan cassette (FIG. 5, lanes 2 and 4). When tested for its ability to utilize different iron-containing compounds, these mutant cells were found to be unable to use hemoglobin-bound iron, regardless of the source (human, bovine, baboon, mouse). The ability of the mutant to utilize hemoglobin-haptoglobin was not tested because the wild-type *N. meningitidis* strain is unable to use haptoglobin-haemoglobin complex as an iron source. However, the mutant was still able to use hemin iron, lactoferrin- and transferrin-bound iron as well as citrate-iron (Table II). As the iron-ontaining component of hemoglobin is hemin, a hemoglobin receptor would be expected to be capable of transporting hemin into the periplasm. Indeed, the cloning strategy disclosed herein depended on the ability of the cloned meningococcal receptor to transport hemin into the periplasm of *E. coli*. These results strongly suggest that *N. meningitidis* has at least two functional receptors that are involved in the internalization of hemin-containing compounds. One is the hemoglobin receptor described herein, which allows the utilization of both hemin and hemoglobin as iron sources. The other putative receptor in *N. meningitidis* is a hemin receptor which allows utilization of only hemin. This schema is also consistent with the isolation of several cosmid clones that allow *E. coli* EB53 to utilize hemin. DNAs from these cosmids do not hybridize with the hmbR probe, indicating that these clones encode a structurally-distinct receptor protein capable of transporting hemin into the periplasm of *N. meningitidis* cells.

EXAMPLE 8

Attenuation of Virulence in hmbR Mutant *N. meningitidis* Cells In Vivo

In order to test the importance of hemoglobin and hemin scavenging systems of *N. meningitidis* in vivo, the hmbR -mutant and the wild type strain were inoculated into 5 day old infant rats and the numbers of bacteria recovered from blood and cerebrospinal fluid were followed. In these experiments, the method for the assessing *N. meningitidis* virulence potential was essentially the same as described by Nassif et al. (1992, ibid.) using infant inbred Lewis rats (Charles River, Saint Aubin les Elbeufs, France). Inbred rats were used to minimize individual variations. Briefly, the 8013 strain was reactivated by 3 animal passages. After the third passage, bacteria were kept frozen in aliquots at −80° C. To avoid the possibility that modifications in the course of infection could result from selection of one spontaneous avirulent variant, one aliquot from the animal-passed frozen stock of 8013 was transformed with chromosomal DNA from the hmbR mutant, the resultant Kan$^r$ transformants were pooled without further purification and kept frozen at −80° C. For each experiment, all infant rats were from the same litter. *N. meningitidis* 8013 was grown overnight and 2×10$^6$ bacteria injected intraperitoneally into the infant rat. Three rats were used for each meningococcal strain. The course of infection was followed over a 24 hours time period with blood collected at the indicated times. At the 24 h time period, the rats were sacrificed, the cerebrospinal fluid (CSF) collected and the number of colony-forming units (CFU) determined. Each experiment was performed in replicate; similar results were obtained both times.

Figure 6:
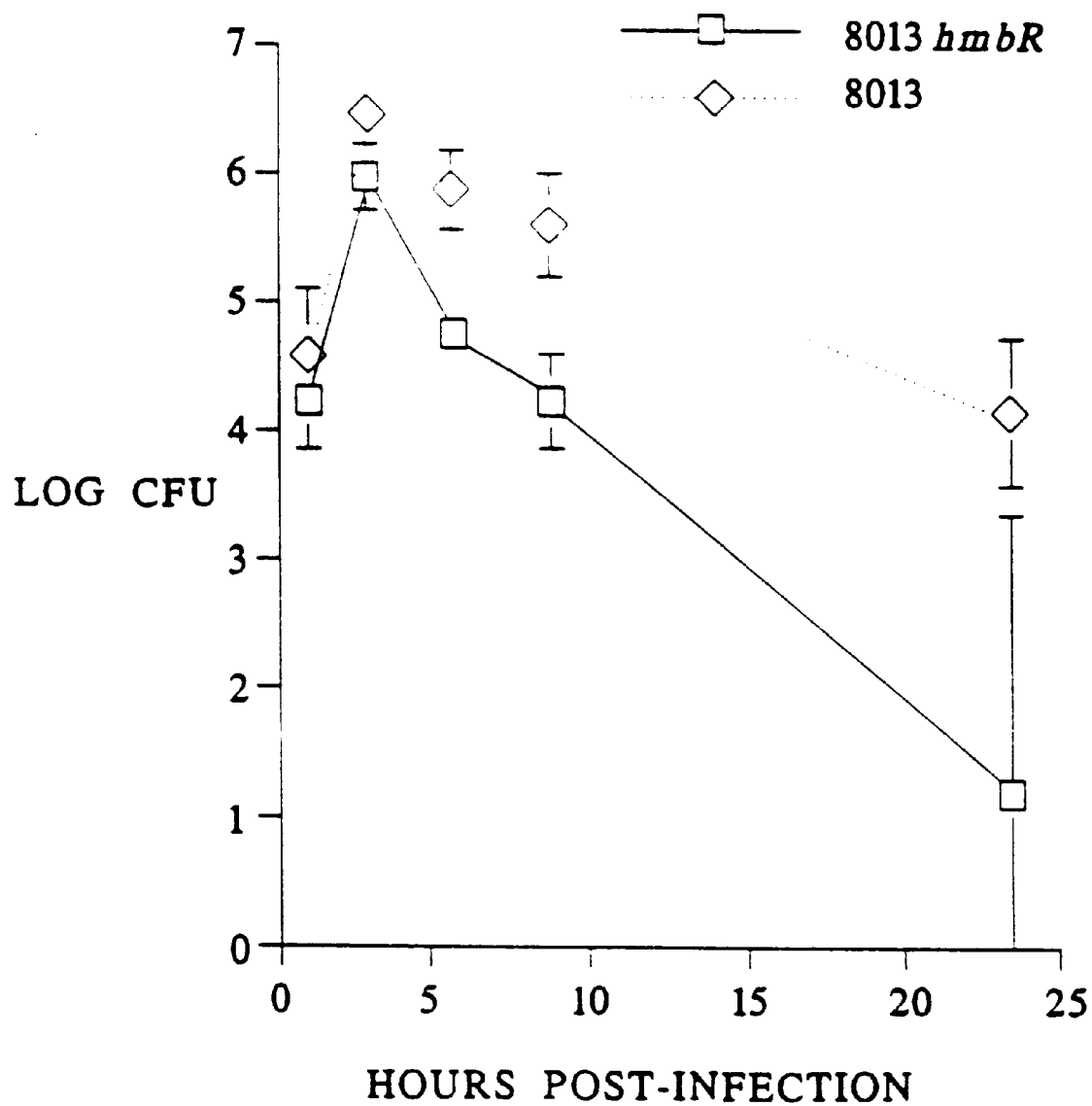
FIG. 6 is a graph describing the course of infection using *N. meningitidis* wild type (MC8013) and hmbR mutant strains in an in vivo rat infant infection model. Each strain was injected intraperitoneally ($2 \times 10^6$ CFU) into three infant inbred Lewis rats. The results represent the average of two similarly-performed experiments.

The results of these experiments are shown in FIG. 6. The hmbR strain, which is unable to use hemoglobin as an iron source, was recovered from the blood of infected animals in significantly lower numbers when compared with the wild type strain. Both the mutant and the wild type strain were still able to cross the blood-brain barrier as indicated by the isolation of bacteria from the cerebrospinal fluid. These results indicate that hemoglobin represents an important iron source for *N. meningitidis* during growth in vivo.

It should be understood that the foregoing disclosure emphasizes certain specific embodiments of the invention and that all modifications or alternatives equivalent thereto are within the spirit and scope of the invention as set forth in the appended claims.

What is claimed is:

1. A vaccine that is effective in providing immunization against an infection of a human with *Neisseria meningitidis* comprising as isolated hemoglobin binding protein having an amino acid sequence identified by Seq. ID No. 2 or an immunogenic fragment thereof, wherein the protein or the immunogenic fragment produces an antibody response in an animal.

* * * * *

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 3318 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (ix) FEATURE:
      (A) NAME/KEY: CDS
      (B) LOCATION: 470..2845

(xi) SEQUENCE DESCRIPTION: SEQ ID NO:1:

```
AGAACTAGTG GATCCAATTT GGGCGCGGCG TTTTTGTTCA AACACGCCCA AAAACTCGAT        60

TACAACGGCG AACACGGCGC GCGCCACCTC GCTCCGCATC CCGACGGGCC GCGGCAAACA       120

CTGGCGCGCC TTCGTCGAGC ATCTGAACGC TTTGAACCTG ACTCCCGAAG CCGAAGCGGA       180

AGCCATTCAA GGCGCGCGCG AAGCCTTTGC ATTCTACAAA GTCGTGTTGC GCGAAACCTT       240

CGGCTTGGCA GCCGATGCCG AAGCCCCCGA AGGTATGATG CCGCACAGGC ACTAAAAAAT       300

AATCGAACCA AATAAACAAG GTCTCGGCAT AGCTGTTTGC AGGGACCTTT AATTACACGG       360

CGCGGCTTTG TTTACATGGA TTACTGTCTT ATTAAATATT AATGATTATC ATAAAATCTA       420

TTATTCGCTA ACCGATGGAT GAACAATCCA TACATCTTGA GTTGATAAT ATG AAA           475
                                                   Met Lys
                                                     1

CCA TTA CAA ATG CTC CCT ATC GCC GCG CTG GTC GGC AGT ATT TTC GGC         523
Pro Leu Gln Met Leu Pro Ile Ala Ala Leu Val Gly Ser Ile Phe Gly
          5                  10                  15

AAT CCG GTC TTT GCG GCA GAT GAA GCT GCA ACT GAA ACC ACA CCC GTT         571
Asn Pro Val Phe Ala Ala Asp Glu Ala Ala Thr Glu Thr Thr Pro Val
     20                  25                  30

AAG GCA GAG GTA AAA GCA GTG CGC GTT AAA GGC CAG CGC AAT GCG CCT         619
Lys Ala Glu Val Lys Ala Val Arg Val Lys Gly Gln Arg Asn Ala Pro
 35                  40                  45                  50

GCG GCT GTG GAA CGC GTC AAC CTT AAC CGT ATC AAA CAA GAA ATG ATA         667
Ala Ala Val Glu Arg Val Asn Leu Asn Arg Ile Lys Gln Glu Met Ile
                 55                  60                  65

CGC GAC AAC AAA GAC TTG GTG CGC TAT TCC ACC GAT GTC GGC TTG AGC         715
Arg Asp Asn Lys Asp Leu Val Arg Tyr Ser Thr Asp Val Gly Leu Ser
             70                  75                  80

GAC AGC GGC CGC CAT CAA AAA GGC TTT GCT GTT CGC GGC GTG GAA GGC         763
Asp Ser Gly Arg His Gln Lys Gly Phe Ala Val Arg Gly Val Glu Gly
         85                  90                  95

AAC CGT GTC GGC GTG AGC ATA GAC GGC GTA AAC CTG CCT GAT TCC GAA         811
Asn Arg Val Gly Val Ser Ile Asp Gly Val Asn Leu Pro Asp Ser Glu
    100                 105                 110

GAA AAC TCG CTG TAC GCC CGT TAT GGC AAC TTC AAC AGC TCG CGT CTG         859
Glu Asn Ser Leu Tyr Ala Arg Tyr Gly Asn Phe Asn Ser Ser Arg Leu
115                 120                 125                 130

TCT ATC GAC CCC GAA CTC GTG CGC AAC ATC GAC ATC GTA AAA GGG GCG         907
Ser Ile Asp Pro Glu Leu Val Arg Asn Ile Asp Ile Val Lys Gly Ala
                135                 140                 145
```

```
GAC TCT TTC AAT ACC GGC AGC GGC GCC TTG GGC GGC GGT GTG AAT TAC      955
Asp Ser Phe Asn Thr Gly Ser Gly Ala Leu Gly Gly Gly Val Asn Tyr
            150                 155                 160

CAA ACC CTG CAA GGA CGT GAC TTA CTG TTG CCT GAA CGG CAG TTC GGC     1003
Gln Thr Leu Gln Gly Arg Asp Leu Leu Leu Pro Glu Arg Gln Phe Gly
            165                 170                 175

GTG ATG ATG AAA AAC GGT TAC AGC ACG CGT AAC CGT GAA TGG ACA AAT     1051
Val Met Met Lys Asn Gly Tyr Ser Thr Arg Asn Arg Glu Trp Thr Asn
        180                 185                 190

ACC CTC GGT TTC GGC GTG AGC AAC GAC CGC GTG GAT GCC GCT TTG CTG     1099
Thr Leu Gly Phe Gly Val Ser Asn Asp Arg Val Asp Ala Ala Leu Leu
195                 200                 205                 210

TAT TCG CAA CGG CGC GGC CAT GAA ACT GAA AGC GCG GGC AAG CGT GGT     1147
Tyr Ser Gln Arg Arg Gly His Glu Thr Glu Ser Ala Gly Lys Arg Gly
                215                 220                 225

TAT CCG GTA GAG GGT GCT GGT AGC GGA GCG AAT ATC CGT GGT TCT GCG     1195
Tyr Pro Val Glu Gly Ala Gly Ser Gly Ala Asn Ile Arg Gly Ser Ala
            230                 235                 240

CGC GGT ATT CCT GAT CCG TCC CAA CAC AAA TAC CAC AGC TTC TTG GGT     1243
Arg Gly Ile Pro Asp Pro Ser Gln His Lys Tyr His Ser Phe Leu Gly
            245                 250                 255

AAG ATT GCT TAT CAA ATC AAC GAC AAC CAC CGC ATC GGC GCA TCG CTC     1291
Lys Ile Ala Tyr Gln Ile Asn Asp Asn His Arg Ile Gly Ala Ser Leu
        260                 265                 270

AAC GGT CAG CAG GGG CAT AAT TAC ACG GTT GAA GAG TCT TAC AAC CTG     1339
Asn Gly Gln Gln Gly His Asn Tyr Thr Val Glu Glu Ser Tyr Asn Leu
275                 280                 285                 290

CTT GCT TCT TAT TGG CGT GAA GCT GAC GAT GTC AAC AGA CGG CGT AAC     1387
Leu Ala Ser Tyr Trp Arg Glu Ala Asp Asp Val Asn Arg Arg Arg Asn
                295                 300                 305

ACC AAC CTC TTT TAC GAA TGG ACG CCG GAA TCC GAC CGG TTG TCT ATG     1435
Thr Asn Leu Phe Tyr Glu Trp Thr Pro Glu Ser Asp Arg Leu Ser Met
            310                 315                 320

GTA AAA GCG GAT GTC GAT TAT CAA AAA ACC AAA GTA TCT GCG GTC AAC     1483
Val Lys Ala Asp Val Asp Tyr Gln Lys Thr Lys Val Ser Ala Val Asn
            325                 330                 335

TAC AAA GGT TCG TTC CCG ATA GAG GAT TCT TCC ACC TTG ACA CGT AAC     1531
Tyr Lys Gly Ser Phe Pro Ile Glu Asp Ser Ser Thr Leu Thr Arg Asn
        340                 345                 350

TAC AAT CAA AAG GAC TTG GAT GAA ATC TAC AAC CGC AGT ATG GAT ACC     1579
Tyr Asn Gln Lys Asp Leu Asp Glu Ile Tyr Asn Arg Ser Met Asp Thr
355                 360                 365                 370

CGC TTC AAA CGC ATT ACC CTG CGT TTG GAC AGC CAT CCG TTG CAA CTC     1627
Arg Phe Lys Arg Ile Thr Leu Arg Leu Asp Ser His Pro Leu Gln Leu
                375                 380                 385

GGG GGG GGG CGA CAC CGC CTG TCG TTT AAA ACT TTC GCC AGC CGC CGT     1675
Gly Gly Gly Arg His Arg Leu Ser Phe Lys Thr Phe Ala Ser Arg Arg
            390                 395                 400

GAT TTT GAA AAC CTA AAC CGC GAC GAT TAT TAC TTC AGC GGC CGT GTT     1723
Asp Phe Glu Asn Leu Asn Arg Asp Asp Tyr Tyr Phe Ser Gly Arg Val
            405                 410                 415

GTT CGA ACC ACC AGC AGT ATC CAG CAT CCG GTG AAA ACC ACC AAC TAC     1771
Val Arg Thr Thr Ser Ser Ile Gln His Pro Val Lys Thr Thr Asn Tyr
        420                 425                 430

GGT TTC TCA CTG TCT GAC CAA ATT CAA TGG AAC GAC GTG TTC AGT AGC     1819
Gly Phe Ser Leu Ser Asp Gln Ile Gln Trp Asn Asp Val Phe Ser Ser
435                 440                 445                 450

CGC GCA GGT ATC CGT TAC GAT CAT ACC AAA ATG ACG CCT CAG GAA TTG     1867
Arg Ala Gly Ile Arg Tyr Asp His Thr Lys Met Thr Pro Gln Glu Leu
```

```
                        455                 460                 465
AAT GCC GAG TGT CAT GCT TGT GAC AAA ACA CCG CCT GCA GCC AAC ACT    1915
Asn Ala Glu Cys His Ala Cys Asp Lys Thr Pro Pro Ala Ala Asn Thr
                470                 475                 480

TAT AAA GGC TGG AGC GGT TTT GTC GGC TTG GCG GCG CAA CTG AAT CAG    1963
Tyr Lys Gly Trp Ser Gly Phe Val Gly Leu Ala Ala Gln Leu Asn Gln
            485                 490                 495

GCT TGG CGT GTC GGT TAC GAC ATT ACT TCC GGC TAC CGT GTC CCC AAT    2011
Ala Trp Arg Val Gly Tyr Asp Ile Thr Ser Gly Tyr Arg Val Pro Asn
        500                 505                 510

GCG TCC GAA GTG TAT TTC ACT TAC AAC CAC GGT TCG GGT AAT TGG CTG    2059
Ala Ser Glu Val Tyr Phe Thr Tyr Asn His Gly Ser Gly Asn Trp Leu
515                 520                 525                 530

CCC AAT CCC AAC CTG AAA GCC GAG CGC ACG ACC ACC CAC ACC CTC TCT    2107
Pro Asn Pro Asn Leu Lys Ala Glu Arg Thr Thr Thr His Thr Leu Ser
                535                 540                 545

CTG CAA GGC CGC AGC GAA AAA GGT ACT TTG GAT GCC AAC CTG TAT CAA    2155
Leu Gln Gly Arg Ser Glu Lys Gly Thr Leu Asp Ala Asn Leu Tyr Gln
            550                 555                 560

AGC AAT TAC CGC AAT TTC CTG TCT GAA GAG CAG AAG CTG ACC ACC AGC    2203
Ser Asn Tyr Arg Asn Phe Leu Ser Glu Glu Gln Lys Leu Thr Thr Ser
        565                 570                 575

GGC GAT GTC AGC TGT ACT CAG ATG AAT TAC TAC TAC GGT ATG TGT AGC    2251
Gly Asp Val Ser Cys Thr Gln Met Asn Tyr Tyr Tyr Gly Met Cys Ser
    580                 585                 590

AAT CCT TAT TCC GAA AAA CTG GAA TGG CAG ATG CAA AAT ATC GAC AAG    2299
Asn Pro Tyr Ser Glu Lys Leu Glu Trp Gln Met Gln Asn Ile Asp Lys
595                 600                 605                 610

GCC AGA ATC CGC GGT CTC GAG CTG ACG GGC CGT CTG AAT GTG GAC AAA    2347
Ala Arg Ile Arg Gly Leu Glu Leu Thr Gly Arg Leu Asn Val Asp Lys
                615                 620                 625

GTA GCG TCT TTT GTT CCT GAG GGC TGG AAA CTG TTC GGC TCG CTG GGT    2395
Val Ala Ser Phe Val Pro Glu Gly Trp Lys Leu Phe Gly Ser Leu Gly
            630                 635                 640

TAT GCG AAA AGC AAA CTG TCG GGC GAC AAC AGC CTG CTG TCC ACC CAG    2443
Tyr Ala Lys Ser Lys Leu Ser Gly Asp Asn Ser Leu Leu Ser Thr Gln
        645                 650                 655

CCG TTG AAA GTG ATT GCC GGT ATC GAC TAT GAA AGT CCG AGC GAA AAA    2491
Pro Leu Lys Val Ile Ala Gly Ile Asp Tyr Glu Ser Pro Ser Glu Lys
    660                 665                 670

TGG GGC GTG TTC TCC CGC CTG ACC TAT CTG GGC GCG AAA AAG GTC AAA    2539
Trp Gly Val Phe Ser Arg Leu Thr Tyr Leu Gly Ala Lys Lys Val Lys
675                 680                 685                 690

GAC GCG CAA TAC ACC GTT TAT GAA AAC AAG GGC TGG GGT ACG CCT TTG    2587
Asp Ala Gln Tyr Thr Val Tyr Glu Asn Lys Gly Trp Gly Thr Pro Leu
                695                 700                 705

CAG AAA AAG GTA AAA GAT TAC CCG TGG CTG AAC AAG TCG GCT TAT GTG    2635
Gln Lys Lys Val Lys Asp Tyr Pro Trp Leu Asn Lys Ser Ala Tyr Val
            710                 715                 720

TTC GAT ATG TAC GGC TTC TAC AAA CCG GTG AAA AAC CTG ACT TTG CGT    2683
Phe Asp Met Tyr Gly Phe Tyr Lys Pro Val Lys Asn Leu Thr Leu Arg
        725                 730                 735

GCA GGC GTA TAT AAT GTG TTC AAC CGC AAA TAC ACC ACT TGG GAT TCC    2731
Ala Gly Val Tyr Asn Val Phe Asn Arg Lys Tyr Thr Thr Trp Asp Ser
    740                 745                 750

CTG CGC GGC CTG TAT AGC TAC AGC ACC ACC AAC TCG GTC GAC CGC GAT    2779
Leu Arg Gly Leu Tyr Ser Tyr Ser Thr Thr Asn Ser Val Asp Arg Asp
755                 760                 765                 770

GGC AAA GGC TTA GAC CGC TAC CGC GCC CCA AGC CGT AAT TAC GCC GTA    2827
```

```
Gly Lys Gly Leu Asp Arg Tyr Arg Ala Pro Ser Arg Asn Tyr Ala Val
            775                 780                 785

TCG CTG GAA TGG AAG TTT TAATCTGGTA TTATTGAATT AATCGCCTTG         2875
Ser Leu Glu Trp Lys Phe
            790

TTGAAAATTA AAGCCGTCCG AATTGTGTTC AAGAACTCAT TCGGACGGTT TTTACCGAAT  2935

CTGTGTGTGG GTTTATAGTG GATTAACAAA AATCAGGACA AGGCGACGAA GCCGCAGACA  2995

GTACAGATAG TACGGAACCG ATTCACTTGG TGAGACCTTT GCAAAATTCC TTTCCCTCCC  3055

GACAGCCGAA ACCCAAACAC AGGTTTTCGG CTGTTTTCGC CCCAAATACC TCCTAATTCT  3115

ACCCAAATAC CCCCTTAATC CTCCCCGATA CCCGATAATC AGGCATCCGG CGCCTTTAGG  3175

CGGCAGCGGG CGCACTTAAC CTGTTTGGCG GCTTCAAAAG GTTCAAACAC ATCGCCTTCA  3235

GGTGGCTTTG CGCACTCACT TTAATCAGTC CGAAATAGGC CGCCCGCGCA TAGCAGAACT  3295

TACGGTGCAG CGTACCGAAC TTT                                         3318

(2) INFORMATION FOR SEQ ID NO:2:

(i) SEQUENCE CHARACTERISTICS:
        (A) LENGTH: 792 amino acids
        (B) TYPE: amino acid
        (D) TOPOLOGY: linear (ii) MOLECULE TYPE: protein (xi) SEQUENCE DESCRIPTION: SEQ ID NO:2:

Met Lys Pro Leu Gln Met Leu Pro Ile Ala Ala Leu Val Gly Ser Ile
  1               5                  10                  15

Phe Gly Asn Pro Val Phe Ala Ala Asp Glu Ala Ala Thr Glu Thr Thr
               20                  25                  30

Pro Val Lys Ala Glu Val Lys Ala Val Arg Val Lys Gly Gln Arg Asn
           35                  40                  45

Ala Pro Ala Ala Val Glu Arg Val Asn Leu Asn Arg Ile Lys Gln Glu
       50                  55                  60

Met Ile Arg Asp Asn Lys Asp Leu Val Arg Tyr Ser Thr Asp Val Gly
 65                  70                  75                  80

Leu Ser Asp Ser Gly Arg His Gln Lys Gly Phe Ala Val Arg Gly Val
                 85                  90                  95

Glu Gly Asn Arg Val Gly Val Ser Ile Asp Gly Val Asn Leu Pro Asp
            100                 105                 110

Ser Glu Glu Asn Ser Leu Tyr Ala Arg Tyr Gly Asn Phe Asn Ser Ser
        115                 120                 125

Arg Leu Ser Ile Asp Pro Glu Leu Val Arg Asn Ile Asp Ile Val Lys
    130                 135                 140

Gly Ala Asp Ser Phe Asn Thr Gly Ser Gly Ala Leu Gly Gly Gly Val
145                 150                 155                 160

Asn Tyr Gln Thr Leu Gln Gly Arg Asp Leu Leu Pro Glu Arg Gln
                165                 170                 175

Phe Gly Val Met Met Lys Asn Gly Tyr Ser Thr Arg Asn Arg Glu Trp
            180                 185                 190

Thr Asn Thr Leu Gly Phe Gly Val Ser Asn Asp Arg Val Asp Ala Ala
        195                 200                 205

Leu Leu Tyr Ser Gln Arg Arg Gly His Glu Thr Glu Ser Ala Gly Lys
    210                 215                 220

Arg Gly Tyr Pro Val Glu Gly Ala Gly Ser Gly Ala Asn Ile Arg Gly
225                 230                 235                 240
```

-continued

```
Ser Ala Arg Gly Ile Pro Asp Pro Ser Gln His Lys Tyr His Ser Phe
            245                 250                 255

Leu Gly Lys Ile Ala Tyr Gln Ile Asn Asp Asn His Arg Ile Gly Ala
            260                 265                 270

Ser Leu Asn Gly Gln Gln Gly His Asn Tyr Thr Val Glu Glu Ser Tyr
            275                 280                 285

Asn Leu Leu Ala Ser Tyr Trp Arg Glu Ala Asp Asp Val Asn Arg Arg
            290                 295                 300

Arg Asn Thr Asn Leu Phe Tyr Glu Trp Thr Pro Glu Ser Asp Arg Leu
305                 310                 315                 320

Ser Met Val Lys Ala Asp Val Asp Tyr Gln Lys Thr Lys Val Ser Ala
                    325                 330                 335

Val Asn Tyr Lys Gly Ser Phe Pro Ile Glu Asp Ser Ser Thr Leu Thr
                    340                 345                 350

Arg Asn Tyr Asn Gln Lys Asp Leu Asp Glu Ile Tyr Asn Arg Ser Met
                    355                 360                 365

Asp Thr Arg Phe Lys Arg Ile Thr Leu Arg Leu Asp Ser His Pro Leu
            370                 375                 380

Gln Leu Gly Gly Gly Arg His Arg Leu Ser Phe Lys Thr Phe Ala Ser
385                 390                 395                 400

Arg Arg Asp Phe Glu Asn Leu Asn Arg Asp Asp Tyr Tyr Phe Ser Gly
                    405                 410                 415

Arg Val Val Arg Thr Thr Ser Ser Ile Gln His Pro Val Lys Thr Thr
                    420                 425                 430

Asn Tyr Gly Phe Ser Leu Ser Asp Gln Ile Gln Trp Asn Asp Val Phe
            435                 440                 445

Ser Ser Arg Ala Gly Ile Arg Tyr Asp His Thr Lys Met Thr Pro Gln
450                 455                 460

Glu Leu Asn Ala Glu Cys His Ala Cys Asp Lys Thr Pro Pro Ala Ala
465                 470                 475                 480

Asn Thr Tyr Lys Gly Trp Ser Gly Phe Val Gly Leu Ala Ala Gln Leu
                    485                 490                 495

Asn Gln Ala Trp Arg Val Gly Tyr Asp Ile Thr Ser Gly Tyr Arg Val
                    500                 505                 510

Pro Asn Ala Ser Glu Val Tyr Phe Thr Tyr Asn His Gly Ser Gly Asn
            515                 520                 525

Trp Leu Pro Asn Pro Asn Leu Lys Ala Glu Arg Thr Thr Thr His Thr
            530                 535                 540

Leu Ser Leu Gln Gly Arg Ser Glu Lys Gly Thr Leu Asp Ala Asn Leu
545                 550                 555                 560

Tyr Gln Ser Asn Tyr Arg Asn Phe Leu Ser Glu Glu Gln Lys Leu Thr
                    565                 570                 575

Thr Ser Gly Asp Val Ser Cys Thr Gln Met Asn Tyr Tyr Gly Met
                    580                 585                 590

Cys Ser Asn Pro Tyr Ser Glu Lys Leu Glu Trp Gln Met Gln Asn Ile
                    595                 600                 605

Asp Lys Ala Arg Ile Arg Gly Leu Glu Leu Thr Gly Arg Leu Asn Val
            610                 615                 620

Asp Lys Val Ala Ser Phe Val Pro Glu Gly Trp Lys Leu Phe Gly Ser
625                 630                 635                 640

Leu Gly Tyr Ala Lys Ser Lys Leu Ser Gly Asp Asn Ser Leu Leu Ser
                    645                 650                 655
```

Thr Gln Pro Leu Lys Val Ile Ala Gly Ile Asp Tyr Glu Ser Pro Ser
            660                 665                 670

Glu Lys Trp Gly Val Phe Ser Arg Leu Thr Tyr Leu Gly Ala Lys Lys
        675                 680                 685

Val Lys Asp Ala Gln Tyr Thr Val Tyr Glu Asn Lys Gly Trp Gly Thr
690                 695                 700

Pro Leu Gln Lys Lys Val Lys Asp Tyr Pro Trp Leu Asn Lys Ser Ala
705                 710                 715                 720

Tyr Val Phe Asp Met Tyr Gly Phe Tyr Lys Pro Val Lys Asn Leu Thr
                725                 730                 735

Leu Arg Ala Gly Val Tyr Asn Val Phe Asn Arg Lys Tyr Thr Thr Trp
            740                 745                 750

Asp Ser Leu Arg Gly Leu Tyr Ser Tyr Ser Thr Thr Asn Ser Val Asp
            755                 760                 765

Arg Asp Gly Lys Gly Leu Asp Arg Tyr Arg Ala Pro Ser Arg Asn Tyr
770                 775                 780

Ala Val Ser Leu Glu Trp Lys Phe
785                 790

(2) INFORMATION FOR SEQ ID NO:3:

(i) SEQUENCE CHARACTERISTICS:
        (A) LENGTH: 602 amino acids
        (B) TYPE: amino acid
        (D) TOPOLOGY: linear (ii) MOLECULE TYPE: protein (xi) SEQUENCE DESCRIPTION: SEQ ID NO:3:

Met Gln Gln Gln His Leu Phe Arg Leu Asn Ile Leu Cys Leu Ser Leu
1               5                   10                  15

Met Thr Ala Leu Pro Val Tyr Ala Glu Asn Val Gln Ala Glu Gln Ala
            20                  25                  30

Gln Glu Lys Gln Leu Asp Thr Ile Gln Val Lys Ala Lys Lys Gln Lys
        35                  40                  45

Thr Arg Arg Asp Asn Glu Val Thr Gly Leu Gly Lys Leu Val Lys Ser
    50                  55                  60

Ser Asp Thr Leu Ser Lys Glu Gln Val Leu Asn Ile Arg Asp Leu Thr
65                  70                  75                  80

Arg Tyr Asp Pro Gly Ile Ala Val Val Glu Gln Gly Arg Gly Ala Ser
                85                  90                  95

Ser Gly Tyr Ser Ile Arg Gly Met Asp Lys Asn Arg Val Ser Leu Thr
            100                 105                 110

Val Asp Gly Val Ser Gln Ile Gln Ser Tyr Thr Ala Gln Ala Ala Leu
        115                 120                 125

Gly Gly Thr Arg Thr Ala Gly Ser Ser Gly Ala Ile Asn Glu Ile Glu
    130                 135                 140

Tyr Glu Asn Val Lys Ala Val Glu Ile Ser Lys Gly Ser Asn Ser Ser
145                 150                 155                 160

Glu Tyr Gly Asn Gly Ala Leu Ala Gly Ser Val Ala Phe Gln Thr Lys
                165                 170                 175

Thr Ala Ala Asp Ile Ile Gly Glu Gly Lys Gln Trp Gly Ile Gln Ser
            180                 185                 190

Lys Thr Ala Tyr Ser Gly Lys Asp His Ala Leu Thr Gln Ser Leu Ala
        195                 200                 205

Leu Ala Gly Arg Ser Gly Gly Ala Glu Ala Leu Leu Ile Tyr Thr Lys

-continued

```
            210                 215                 220
Arg Arg Gly Arg Glu Ile His Ala His Lys Asp Ala Gly Lys Gly Val
225                 230                 235                 240

Gln Ser Phe Asn Arg Leu Pro Ile Cys Arg Phe Gly Asn Asn Thr Tyr
                245                 250                 255

Thr Asp Cys Thr Pro Arg Asn Ile Gly Gly Asn Gly Tyr Tyr Ala Ala
                260                 265                 270

Val Gln Asp Asn Val Arg Leu Gly Arg Trp Ala Asp Val Gly Ala Gly
                275                 280                 285

Ile Arg Tyr Asp Tyr Arg Ser Thr His Ser Glu Asp Lys Ser Val Ser
                290                 295                 300

Thr Gly Thr His Arg Asn Leu Ser Trp Asn Ala Gly Val Val Leu Lys
305                 310                 315                 320

Pro Phe Thr Trp Met Asp Leu Thr Tyr Arg Ala Ser Thr Gly Phe Arg
                325                 330                 335

Leu Pro Ser Phe Ala Glu Met Tyr Gly Trp Arg Ala Gly Glu Ser Leu
                340                 345                 350

Lys Thr Leu Asp Leu Lys Pro Glu Lys Ser Phe Asn Arg Glu Ala Gly
                355                 360                 365

Ile Val Phe Lys Gly Asp Phe Gly Asn Leu Glu Ala Ser Tyr Phe Asn
                370                 375                 380

Asn Ala Tyr Arg Asp Leu Ile Ala Phe Gly Tyr Glu Thr Arg Thr Gln
385                 390                 395                 400

Asn Gly Gln Thr Ser Ala Ser Gly Asp Pro Gly Tyr Arg Asn Ala Gln
                405                 410                 415

Asn Ala Arg Ile Ala Gly Ile Asn Ile Leu Gly Lys Ile Asp Trp His
                420                 425                 430

Gly Val Trp Gly Gly Leu Pro Asp Gly Leu Tyr Ser Thr Leu Ala Tyr
                435                 440                 445

Asn Arg Ile Lys Val Lys Asp Ala Asp Ile Arg Ala Asp Arg Thr Phe
450                 455                 460

Val Thr Ser Tyr Leu Phe Asp Ala Val Gln Pro Ser Arg Tyr Val Leu
465                 470                 475                 480

Gly Leu Gly Tyr Asp His Pro Asp Gly Ile Trp Gly Ile Asn Thr Met
                485                 490                 495

Phe Thr Tyr Ser Lys Ala Lys Ser Val Asp Glu Leu Leu Gly Ser Gln
                500                 505                 510

Ala Leu Leu Asn Gly Asn Ala Asn Ala Lys Lys Ala Ser Arg Arg
                515                 520                 525

Thr Arg Pro Trp Tyr Val Thr Asp Val Ser Gly Tyr Tyr Asn Ile Lys
                530                 535                 540

Lys His Leu Thr Leu Arg Ala Gly Val Tyr Asn Leu Leu Asn Tyr Arg
545                 550                 555                 560

Tyr Val Thr Trp Glu Asn Val Arg Gln Thr Ala Gly Gly Ala Val Asn
                565                 570                 575

Gln His Lys Asn Val Gly Val Tyr Asn Arg Tyr Ala Ala Pro Gly Arg
                580                 585                 590

Asn Tyr Thr Phe Ser Leu Glu Met Lys Phe
                595                 600
```

(2) INFORMATION FOR SEQ ID NO:4:

(i) SEQUENCE CHARACTERISTICS:
        (A) LENGTH: 607 amino acids (B) TYPE: amino acid
(D) TOPOLOGY: linear (ii) MOLECULE TYPE: protein (xi) SEQUENCE DESCRIPTION: SEQ ID NO:4:

```
Met Asn Lys Lys His Gly Phe Gln Leu Thr Leu Thr Ala Leu Ala Val
 1               5                  10                  15

Ala Ala Ala Phe Pro Ser Tyr Ala Ala Asn Pro Glu Thr Ala Ala Pro
             20                  25                  30

Asp Ala Ala Gln Thr Gln Ser Leu Lys Glu Val Thr Val Arg Ala Ala
         35                  40                  45

Lys Val Gly Arg Arg Ser Lys Glu Ala Thr Gly Leu Gly Lys Ile Ala
     50                  55                  60

Lys Thr Ser Glu Thr Leu Asn Lys Glu Gln Val Leu Gly Ile Arg Asp
 65                  70                  75                  80

Leu Thr Arg Tyr Asp Pro Gly Val Ala Val Val Glu Gln Gly Asn Gly
                 85                  90                  95

Ala Ser Gly Gly Tyr Ser Ile Arg Gly Val Asp Lys Asn Arg Val Ala
            100                 105                 110

Val Ser Val Asp Gly Val Ala Gln Ile Gln Ala Phe Thr Val Gln Gly
        115                 120                 125

Ser Leu Ser Gly Tyr Gly Gly Arg Gly Gly Ser Gly Ala Ile Asn Glu
    130                 135                 140

Ile Glu Tyr Glu Asn Ile Ser Thr Val Glu Ile Asp Lys Gly Ala Gly
145                 150                 155                 160

Ser Ser Asp His Gly Ser Gly Ala Leu Gly Gly Ala Val Ala Phe Arg
                165                 170                 175

Thr Lys Glu Ala Ala Asp Leu Ile Ser Asp Gly Lys Ser Trp Gly Ile
            180                 185                 190

Gln Ala Lys Thr Ala Tyr Gly Ser Lys Asn Arg Gln Phe Met Lys Ser
        195                 200                 205

Leu Gly Ala Gly Phe Ser Lys Asp Gly Trp Glu Gly Leu Leu Ile Arg
    210                 215                 220

Thr Glu Arg Gln Gly Arg Glu Thr His Pro His Gly Asp Ile Ala Asp
225                 230                 235                 240

Gly Val Ala Tyr Gly Ile Asn Arg Leu Ser Val Cys Gly Tyr Ile Glu
                245                 250                 255

Thr Leu Arg Ser Arg Lys Cys Val Pro Arg Lys Ile Asn Gly Ser Asn
            260                 265                 270

Ile His Ile Ser Leu Asn Asp Arg Phe Ser Ile Gly Lys Tyr Phe Asp
        275                 280                 285

Phe Ser Leu Gly Gly Arg Tyr Asp Arg Lys Asn Phe Thr Thr Ser Glu
    290                 295                 300

Glu Leu Val Arg Ser Gly Arg Tyr Val Asp Arg Ser Trp Asn Ser Gly
305                 310                 315                 320

Ile Val Phe Lys Pro Asn Arg His Phe Ser Leu Ser Tyr Arg Ala Ser
                325                 330                 335

Ser Gly Phe Arg Thr Pro Ser Phe Gln Glu Leu Phe Gly Ile Asp Ile
            340                 345                 350

Tyr His Asp Tyr Pro Lys Gly Trp Gln Arg Pro Ala Leu Lys Ser Glu
        355                 360                 365

Lys Ala Ala Asn Arg Glu Ile Gly Leu Gln Trp Lys Gly Asp Phe Gly
    370                 375                 380
```

-continued

```
Phe Leu Glu Ile Ser Ser Phe Arg Asn Arg Tyr Thr Asp Met Ile Ala
385                 390                 395                 400

Val Ala Asp His Lys Thr Lys Leu Pro Asn Gln Ala Gly Gln Leu Thr
                405                 410                 415

Glu Ile Asp Ile Arg Asp Tyr Tyr Asn Ala Gln Asn Met Ser Leu Gln
            420                 425                 430

Gly Val Asn Ile Leu Gly Lys Ile Asp Trp Asn Gly Val Tyr Gly Lys
        435                 440                 445

Leu Pro Glu Gly Leu Tyr Thr Thr Leu Ala Tyr Asn Arg Ile Lys Pro
    450                 455                 460

Lys Ser Val Ser Asn Arg Pro Gly Leu Ser Leu Arg Ser Tyr Ala Leu
465                 470                 475                 480

Asp Ala Val Gln Pro Ser Arg Tyr Val Leu Gly Phe Gly Tyr Asp Gln
                485                 490                 495

Pro Glu Gly Lys Trp Gly Ala Asn Ile Met Leu Thr Tyr Ser Lys Gly
            500                 505                 510

Lys Asn Pro Asp Glu Leu Ala Tyr Leu Ala Gly Asp Gln Lys Arg Tyr
        515                 520                 525

Ser Thr Lys Arg Ala Ser Ser Ser Trp Ser Thr Ala Asp Val Ser Ala
    530                 535                 540

Tyr Leu Asn Leu Lys Lys Arg Leu Thr Leu Arg Ala Ala Ile Tyr Asn
545                 550                 555                 560

Ile Gly Asn Tyr Arg Tyr Val Thr Trp Glu Ser Leu Arg Gln Thr Ala
                565                 570                 575

Glu Ser Thr Ala Asn Arg His Gly Gly Asp Ser Asn Tyr Gly Arg Tyr
            580                 585                 590

Ala Ala Pro Gly Arg Asn Phe Ser Leu Ala Leu Glu Met Lys Phe
        595                 600                 605

(2) INFORMATION FOR SEQ ID NO:5:

(i) SEQUENCE CHARACTERISTICS:
          (A) LENGTH: 7 amino acids
          (B) TYPE: amino acid
          (D) TOPOLOGY: linear (ii) MOLECULE TYPE: peptide (xi) SEQUENCE DESCRIPTION: SEQ ID NO:5:

Glu Thr Thr Pro Val Lys Ala
```